United States Patent [19]

Brandenburger

[11] Patent Number: 4,926,870

[45] Date of Patent: May 22, 1990

[54] METHOD AND APPARATUS FOR ULTRASONIC ANALYSIS OF BONE STRENGTH IN VIVO

[75] Inventor: Gary H. Brandenburger, Maynard, Mass.

[73] Assignee: Osteo-Technology, Inc., Cambridge, Mass.

[21] Appl. No.: 238,282

[22] Filed: Aug. 30, 1988

[51] Int. Cl.$^5$ ............................................... A61B 8/00
[52] U.S. Cl. ................................ 128/660.01; 73/597
[58] Field of Search ..................... 128/660.01, 660.06, 128/661.03; 73/597–599

[56] References Cited

U.S. PATENT DOCUMENTS

| | | | |
|---|---|---|---|
| 2,439,130 | 4/1948 | Firestone | 73/598 |
| 3,477,422 | 11/1969 | Jurist, Jr. et al. | 128/660.01 |
| 3,664,180 | 5/1972 | McDonald | 73/598 |
| 3,713,329 | 1/1973 | Munger | 128/661.05 |
| 3,847,141 | 11/1974 | Hoop | 128/660.01 |
| 4,048,986 | 9/1977 | Ott | 128/660.01 |
| 4,138,999 | 2/1979 | Eckhart et al. | 128/661.05 |
| 4,233,845 | 11/1980 | Pratt | 128/660.01 |
| 4,361,154 | 11/1982 | Pratt, Jr. | 128/660.01 |
| 4,421,119 | 12/1983 | Pratt, Jr. | 128/660.01 |
| 4,774,959 | 10/1988 | Palmer et al. | 73/599 X |
| 4,807,635 | 2/1989 | Ophir | 73/597 X |

FOREIGN PATENT DOCUMENTS 219853 5/1966 U.S.S.R. .

*Primary Examiner*—Francis Jaworski
*Attorney, Agent, or Firm*—Finnegan, Henderson, Farabow, Garrett & Dunner

[57] ABSTRACT

An apparatus and a method are provided for directing an ultrasonic signal along a desired path through a member and for establishing the strength of the member. A transmitter sends an ultrasonic signal through the member that is received by a receiver and a conditioned electronic waveform is generated that is representative of the received waveform. Selected characteristics of the conditioned electronic waveform are compared with corresponding characteristics of a canonical waveform, the canonical waveform being obtained when ultrasonic signals propagate along the desired path through the member. When the selected characteristics of the conditioned electronic waveform are substantially the same as the corresponding characteristics of the canonical waveform, the ultrasonic signal has propagated at least along the desired path. The apparent velocity of the ultrasonic signal that propagates along the desired path is computed and is related to bone strength.

32 Claims, 12 Drawing Sheets

METHOD AND APPARATUS FOR ULTRASONIC ANALYSIS OF BONE STRENGTH IN VIVO

BACKGROUND OF THE INVENTION

1. Field of the Invention

The present invention relates to non-invasive apparatuses and methods for determining bone strength in vivo and, most particularly, to such apparatuses and methods that use ultrasonic energy for determining bone strength in vivo.

2. Discussion of Related Art

Osteoporosis is a complex, incompletely understood disease that affects the entire skeletal system. Herein, the term "osteoporosis" is used to refer to a variety of conditions all characterized by a degradation of bone strength ultimately leading to fracture.

To understand bone strength, one must understand bone architecture and composition. Although all bones comprise the same structural constituents of collagen, crystallized calcium and interstitial fluid, individual bones have architectures that differ significantly. The skeletal system can be generally divided into two categories of bones: cortical (compact) bone and cancellous (spongy) bone. Most bones in the body contain both categories, the compact cortical bone forming an outer shell surrounding a core of spongy cancellous bone. Cancellous bone is in the form of a three-dimensional lattice made of plates and columns (called trabeculae), and an interstitial fluid composed of red and yellow marrow and traces of other substances.

Recent research suggests that the deterioration of the mechanical strength of bone results from three different, yet interrelated, mechanisms. First, and most widely recognized, is the loss of bone mass which occurs in all individuals beginning in the third decade of life. The literature conclusively demonstrates the diminution of bone strength with loss of bone mass. See. e.g., Goldstein, S. A., "The Mechanical Properties of Trabecular Bone: Dependence on Anatomic Location and Function," J.Biomechanics, vol. 20, No. 11/12. pp. 1055–1061, 1987.

The second potentially important mechanism for deterioration of bone strength is the deterioration of the quality of the bone matrix itself. Recently discovered evidence suggests that biochemical stability of collagen in trabecular bone declines with age. See, Oxlund, H., Mosekilde, L., Ortoft, G., "Alterations in the Stability of Collagen from Human Trabecular Bone with Respect to Age," (abstract #97), Proceedings of the International Symposium on Osteoporosis, Ed., J. Jensen, B. Riis, C. Christiansen, Aalborg, Denmark, September 27–October 2, 1987. Furthermore, the collagen content of trabecular bone appears to be reduced in women with osteoporosis. Birkenhaager, D. H., "A Significant Lack of Collagen in Osteoporotic Bone," (abstract #111), Proceedings of the International Symposium on Osteoporosis, Ed., J. Jensen, B. Riis, C. Christiansen, Aalborg, Denmark, September 27–October 2, 1987. These references suggest a weakening of the protein binding the trabecular matrix, irrespective of bone mass. The strength of bone is crucial in determining whether a person will suffer osteoporotic fracture in the absence of trauma.

A third mechanism for the deterioration of bone strength has been identified as osteoporosis-related changes in trabecular architecture, even when accompanied by little or no measurable loss of bone mass. See, e.g., Kleerekoper, M., et al., "The Role of Three-Dimensional Trabecular Microstructure in the Pathogenesis of Vertebral Compression Fractures," Calcif. Tissue Int., 37:594–597, 1985.

These references identify three aspects of osteoporosis related changes in bone architecture. The first is unrepaired fatigue damage, fatigue being caused by repeated cyclings of stress on a bone. Such repeated cyclings cause fatigue damage and the strength of the bone is degraded when such fatigue damage is not repaired. Incomplete repair of fatigue damage can further decrease bone strength when damaged bone has been resorbed but not yet replaced with new bone. The second is deterioration of trabecular architecture, such as a decrease in the number of trabeculae between plates in cancellous bone which occurs in some women during menopause. The third is osteoid accumulation which is a result of collagen exhibiting a lack of calicification. None of these factors that degrade the strength of bone is necessarily characterized by a loss of bone mass. For example, the loss of trabecular columns between trabecular plates appears to reduce bone strength more than can be accounted for by a loss of bone mass alone.

In the past, various practices have been employed for the detection and evaluation of bone disease. Practice patterns vary regionally and by medical speciality. Physician specialists in obstetrics, gynecology, endocrinology, nutrition, internal medicine, orthopedics, radiology, nuclear medicine, family and general practice see and take an interest in bone disease. Depending upon their interests, such physicians may use some or all of the following bone health assessment techniques.

One assessment technique is a physical exam in which particular attention is paid to the structure of the spine. Complaints of sharp back pain and/or obvious curvature (kyphosis) is symptomatic of later stages of bone diseases, such as osteoporosis.

A second assessment technique is risk factor assessment in which a patient's medical and family history is surveyed and/or personal habits, such as smoking, alcohol consumption and diet, are analyzed to assess the relative risk of osteoporotic fracture. Although widely considered a possibility, conclusive evidence of the predominance of particular risk factors as predictors of bone disease is unsubstantiated. J. T. Citron, et al., "Prediction of Peak Prememenopausal Bone Mass Using a Scale of Weighted Clinical Variables," Proceedings of the International Symposium on Osteoporosis, September/October, 1987, Denmark, Editors: J. Jensen, B. Riis, C. Christiansen, Abstract #17.

A third assessment technique involves blood and urine chemistries in which chemical analysis of blood and urine is conducted to determine the presence of calcium and other factors related to bone metabolism. Although clearly related to bone metabolism, such chemistries are not necessarily indicative of bone strength.

A fourth method involves bone mass measuring techniques which measures radiation passed through all or a desired portion of a skeletal system as an indication as to the bone mass density of the bone being tested. Such bone mass measurement techniques are described in Peck, et al., "Physicians Resource Manual On Osteoporosis: A Decision Making Guide," National Osteoporosis Foundation, pp. 14–16, 1987, and include X-ray, single photon absorptiometry, dual photon absorptiometry and quantitative computed tomography.

Although the foregoing techniques do provide information about bones in vivo, they provide insufficient information to determine the strength of bone reliably in all cases. For example, the bone mass measuring techniques provide information concerning the mass of the bone but not its architecture and both factors are important in assessing the strength of a bone. A more effective assessment of osteoporotic fracture risk requires a more direct assessment of strength of bone. This is the motivation for the ultrasonic measurement of bone strength.

Sound is a traveling mechanical vibration. As it propagates, the vibration interacts with the mechanical properties of the medium and becomes progressively altered. By observing the differences between mechanical vibrations transmitted into bone and the mechanical vibrations after an ultrasonic signal has propagated a known distance through the bone, it is often possible to determine some of the mechanical properties of the bone.

Before discussing the specific application of ultrasound to the measurement of bone strength, it is important to review certain underlying physical concepts. Strain in a particular direction (which will be denoted as "X"), is the deformation an object exhibits when subjected to stress in that particular direction (which will be denoted as "F"). For example, strain X can be expressed as the percentage by which a bone shortens when compressed by force F. The elastic modulus E, associated with that particular direction, simply tells how much an object will deform when subjected to a specific amount of stress (F). The elastic modulus E is large for a strong object which exhibits little strain when subjected to a large force F. A weak object has a small elastic modulus E and will exhibit a large strain even when a small stress is applied. The three values can be related as follows:

$$E = \frac{F}{X} \quad (1)$$

When a bone, having a constant elastic modulus E, is subjected to a stress F in a particular direction it deforms by the amount X in that same direction as determined by equation 1, so long as the stress is not so large as to cause plastic deformation or permanent alteration of the bone. The onset of fracture is that level of strain for which the bone no longer returns to its original state when the stress causing the strain is removed. A fracture can be either an outright break or the more subtle damage of stress fracture. $X_T$ is this threshold value of strain at which fracture begins to occur. $F_T$ is the corresponding stress leading to this strain. Then, from the stress/strain relationship above:

$$F_T = E^* X_T \quad (2)$$

To predict imminent fracture of a bone, one must determine either: (a) whether the maximum strain which the bone will exhibit as a result of the environment will exceed $X_T$; or (b) whether the maximum stress experienced as a result of the environment will exceed $F_T$. Of course, predicting imminent fracture with either of these bone characteristics is academic since one cannot determine $F_T$ or $X_T$. Similarly, one cannot measure the maximum stress that a subject's activities will cause or the maximum deformation that will result.

An alternative approach is to note that as a bone becomes weaker, it will exhibit greater strain X when subjected to a given stress F than will a stronger bone subjected to the same stress. The elastic modulus E should therefore decline as a bone becomes weaker. The elastic modulus can therefore be taken as an important component of a bone's likelihood to fracture.

The mechanics of solids relate the velocity of an ultrasonic signal to the stress/strain relationship discussed above. The velocity of longitudinal sound V in a given direction through a solid such as bone is:

$$V = \sqrt{\frac{E}{r}} \quad (3)$$

where E is the elastic modulus in the direction under consideration; and r is the mass density of bone expressed, for example, in units of grams/cc. See, Abendschein, W., Hyatt, G. W., "Ultrasonic and Selected Physical Properties of Bone," Clin. Orthop. Rel. Res., 69:294-301, 1970.

Aging and certain diseases cause a decline in both the bone density r and the bone strength. Deterioration in bone strength is manifest as a decline in elastic modulus E. There is still insufficient information in equation 3, however, to tell how the velocity of sound will change in the face of deteriorating bone condition.

What is missing is the relationship between the elastic modulus E and the density r in bone. The elastic modulus has been shown empirically to be proportional to the square of the density r:

$$E = K^* r^2 \quad (4)$$

See, e.g., Rice, J. C., Cowin, S. C., Bowman, J. A., "On The Dependence of the Elasticity and Strength of Cancellous Bone on Apparent Density," J. Biomechanics (in press), 1988.

The proportionality constant K has a physical interpretation. The primary structural constituents of bone are collagen fibrils, crystallized calcium (apatite), and an interstitial viscous fluid (marrow). Different relative proportions of each result in different values for the density. However, as discussed above, for a particular density r the same region of the same bone in different individuals (or the same individual at different stages of life) can possess different bone strengths; that is, the bone can have the same density r but different elastic modulus E. This is accounted for by a different bone quality factor K.

Much of this difference lies in the microscopic architecture of the bone itself. See, e.g., M. Kleerekoper, et al., "The Role of Three-Dimensional Trabecular Microstructure in the Pathogenesis of Verterbral Compression Fractures," Calcif. Tissue Int., 37:594-597, 1985. For example, one can pulverize bone and then compact it into a cylindrical shape to create a very high density object with almost no strength at all. Indeed, for a time after suffering a fracture associated with osteoporosis, crushed vertebra often exhibit higher mass density than adjacent normal vertebra when measured with X-ray, CT or dual photon devices. See, Hui, S. L., Slemenda, C. W., Johnston, C. C., Appledorn, C. R., "Effects of Age and Menopaure on Vertrebal Bone Density," Bone and Mineral, 2:141-146, 1987 and Ott, S. M., "Noninvasive Measurements of Bone Mass," *Osteoporosis: Current Concepts,* Report of the 7th Ross Another potentially important determinant of the bone quality factor K is the quality of the bone matrix itself. As explained above, the biochemical stability of collagen in trabecular bone declines with age. Furthermore, the collagen content of trabecular bone appears to be lower in women with osteoporosis. Both results suggest a weakening of the protein binding the trabecular matrix. Still further, bone quality factor K deteriorates as a result of unrepaired fatigue damage or osteoid accumulation.

The bone quality factor K, then, appears to be a measure of structural quality, indicating bone architecture and the quality of the bone matrix. For a given density r, the higher the bone quality factor K, the stronger the bone.

To understand how this relates to ultrasound, substitute the equation four (4) for the elastic modulus E in the expression for the velocity of sound V in equation (3). The elastic modulus E then disappears leaving:

$$V = \sqrt{K^*r} \qquad (5)$$

Now it becomes clear that bone deterioration resulting in a decrease in either the bone quality factor K or density r causes a decrease in the velocity V, because the mass density r no longer appears in a denominator as it did in the earlier expression for velocity V.

Radiological devices that measure only the density r of bone yield only part of the information needed to characterize the mechanical properties of bone. No information about the physical architecture of the bone is present. In contrast, the velocity of sound yields a quantity related to both the density r and the structural quality as represented by the bone quality factor K.

It appears, then, that the velocity by itself can serve as a measure of bone quality. Further, the velocity might also serve as an approximate indicator of the susceptibility of a bone to fracture. However, the accuracy of any indicator will be compromised by other uncontrollable factors which are difficult to quantify. See, Wasnich, R. D., "Fracture Prediction With Bone Mass Measurements," *Osteoporosis Update* 1987, Ed., H. K. Genant, Radiology Research and Education Foundation, San Francisco, CA, 95–101, 1987. These uncontrollable factors include, for example, range of physical activity of the individual; muscle tone; loss of coordination; the environment (for example, frequent walks on icy stairs); and general health. Thus, the clinician must evaluate all factors concurrently rather than relying upon a single measure.

The velocity of sound propagation has been used successfully to characterize the elastic modulus and breaking strength of engineering materials. Recognizing the potential for application to bone disease, bone biomechanics researchers have shown conclusively that the velocity of sound can be used to assess the elastic modulus and breaking strength of bone, in-vitro. See, W. Abendschein, Hyatt, G. W., "Ultrasonic and Selected Physical Properties of Bone," Clin. Orthop. Rel. Res., 69:294–301, 1970; Ashman, R. B., Cowin, S. C., Van Buskirk, W. C., Rice, J. C., "A Continuous Wave Technique for the Measurement of the Elastic Properties of Cortical Bone," J. Biomechanics, 17(5):349–361, 1984; Ashman, R. B., Rosina, G., Cowin, S. C., Fontenot, M. G., "The Bone Tissue of the Canine Mandible is Elastically Isotropic," J. Biomechanics, 18(9):717–721, 1985; and Ashman, R. B., Corin, J. D., Turner, C. H., "Elastic Properties of Cancellous Bone: Measurement by an Ultrasonic Technique," J. Biomechanics, 20(10):979–986, 1987.

Despite the success of in vitro characterization of bone with velocity, successful in vivo application has remained elusive. Early attempts were made to infer the velocity of long bones from measurements of the frequency of bulk resonance. See, Jurist, J. M., "In Vivo Determination of the Elastic Response of Bone I. Method of Ulnar Resonant Frequency Determination," Phys. Med. Biol., 15(3) 417–426. 1970; Jurist, J. M., "In Vivo Determination of the Elastic Response of Bone II. Ulnar Resonant Frequency in Osteoporotic, Diabetic and Normal Subjects," Phys. Med. Biol., 15(3):427–434, 1970; Fujita, T., et al., "Basic and Clinical Evaluation of the Measurement of Bone Resonant Frequency," Calcif. Tissue Int., 35:153–158, 1983. Only limited success was achieved due to difficulty in controlling major sources of error such as muscle tension, amount of fat and muscle tissue, and complexity of the shape of the long bone. Also, X-ray assessment of the size of the bone was required to accurately determine the length of long bones as a prerequisite to accurate velocity measurements.

More success was achieved with the development of methods for direct measurement of the velocity in peripheral bones. This work began with detection of stress fracture in the metacarpal and metatarsal bones in horses to intervene in the training of race horses before serious fracture occurred. See, e.g., Pratt, G. W., "An In Vivo Method of Ultrasonically Evaluating Bone Strength," Proc. Amer. Assoc. Equine Pract. 26:295–306, 1980; Rabin, D. S., et al., "The Clinical Use of Bone Strength Assessment in the Thoroughbred Race Horse," Proc. Amer. Assoc. Equine Pract., 29:343–351, 1983; and Jeffcot, L. B., et al., "Ultrasound as a Tool for Assessment of Bone Quality in the Horse," Vet. Record, 116:337–342, 1985.

A relationship between the quality of bone and ultrasonic velocity in humans was demonstrated in runners in the 26 mile Boston Marathon. Rubin, C. T., et al., "The Use of Ultrasound In Vivo to Determine Acute Change in the Mechanical Properties of Bone Following Intense Physical Activity," J. Biomechanics, 20(7):723–727, 1987.

A potential clinical application in humans was demonstrated in a study of bone status in premature newborn infants. Wright, L. W., Glade, M. J., Gopal, J., "The Use of Transmission Ultrasonics to Assess Bone Status in the Human Newborn," Pediatric Research, 22(5):541–544, 1987. The study had two components. First, the apparent velocity measured in situ was compared with bone-mineral content (BMC), gestational age and breaking strength in vitro in post-mortem newborns. Second, newborn infants were followed with BMC and ultrasonic analysis. The study demonstrated that velocity of an ultrasonic signal increased linearly with gestational age and correlated well with BMC and breaking strength.

The work disclosed in Gilbert et al., "Correlation Between Transmission Ultrasound and Bone Mass Quantitation Techniques in Postmenopausal Osteoporosis," (abstract), Proc. 33rd Meeting, Soc. Nucl. Med., June, 1986, in which certain teachings of U.S. Pat. No. 4,421,119 to Pratt were used, shows a correlation of ultrasonic velocity of the patella with mass density measured in the spine and wrist.

Although the foregoing methods did indicate that ultrasonic measurement in vivo of bone strength has potential utility, there was no disclosure or suggestion of a device that has clinical utility. Currently available ultrasonic, in vivo bone strength measurement methods are neither accurate nor repeatable. It is important to note that there appears to be a difference of at most 15% in the velocity of cancellous bone, such as the patella, between younger non-osteoporotic and older osteoporotic subjects. Further, the velocity measured in a single bone, such as the patella, varies on the order of 15% depending upon the position of the path of propagation of the wave within the bone. Thus, with present techniques it cannot be predictably determined whether a given result is occasioned by osteoporosis or by variabilities associated with the operation of the measurement equipment.

In addition, currently available techniques do not consider the anisotropic and inhomogenous nature of bone and the number of paths between a sending and receiving transducer that an ultrasonic wave traverses. At present, techniques do not differentiate between paths. Thus, it is an object of the present invention to provide a method and apparatus for locating a desired path through a member, such as a bone, in vivo, and directing an ultrasonic signal along the desired path. It is further an object of the present invention to receive a component of an ultrasonic signal that propagates along a desired path, distinguish it from other components and determine its velocity to provide information about the strength of the member.

SUMMARY OF THE INVENTION

Additional objects and advantages of the invention will be set forth in part in the description which follows, and in part will be obvious from the description, or may be learned by practice of the invention. The objects and advantages of the invention may be realized and attained by the instrumentalities and combinations particularly pointed out in the appended claims.

The present invention overcomes the problems and disadvantages of the prior art by providing a method and apparatus for in vivo ultrasonic analysis of bone which is capable of repeatable and accurate determination of the velocity of an ultrasonic wave along a desired path in a bone in vivo. The present invention takes into consideration the anisotropic and inhomogenous nature of bone and the result that an ultrasonic signal traverses a number of paths through bone.

To achieve the objects and in accordance with the purpose of the invention, as embodied and broadly described herein, a method is provided for directing an ultrasonic signal along a desired path through a member and for determining the stength of the member. The ultrasonic signal is capable of propagating along a plurality of ultrasonic paths, including the desired ultrasonic path through the member. The member interacts with ultrasonic signals differently along each of the plurality of paths.

The method of the present invention includes the step of positioning an ultrasonic transmitter and an ultrasonic receiver proximate the member to establish a direct ultrasonic path between said transmitter and said receiver approximately along said desired path. An ultrasonic signal is launched into the member toward the receiver and received after it propagates through the member. A received electronic signal is then produced which is representative of the ultrasonic signal received by the receiver.

In the next step, signal conditioning of the received electronic signal is performed to produce a conditioned electronic waveform. Then, selected characteristics of the conditioned electronic waveform are compared with corresponding selected characteristics of a canonical waveform, the canonical waveform being obtained due to the interaction of the member with the launched ultrasonic signal as the launched ultrasonic signal propagates at least along the desired path through the member.

The transmitter and the receiver are continuously repositioned at different orientations relative to the member to establish different ultrasonic pathways until the selected characteristics of the conditioned electronic waveform are substantially the same as the selected characteristics of the canonical waveform, thereby indicating that the ultrasonic signal launched from the transmitter has propagated along at least the desired path to said receiver.

A propagation time for the component of the ultrasonic signal that propagates through the member along the desired path is then computed as the time elapsed between launching the ultrasonic signal and receiving the component of the received ultrasonic signal that propagates through the member along the desired path.

The apparent velocity of the component of the received ultrasonic signal that propagates through the member along the desired path can be computed by dividing a determined distance between the receiver and the transmitter by the measured propagation time. The apparent velocity is related to the strength of the member.

The present invention also involves an apparatus for directing an ultrasonic signal along a desired ultrasonic path through a member to establish the strength of the member. The ultrasonic signal is capable of propagating along a plurality of ultrasonic paths with the member interacting with the ultrasonic signal differently along each of the plurality of paths.

The apparatus of the present invention includes an ultrasonic transmitter and an ultrasonic receiver positioned proximate the member to establish a direct ultrasonic path between the transmitter and the receiver approximately along the desired path. The transmitter includes means for launching a launched ultrasonic signal into the member toward the receiver, and the receiver includes means for receiving the launched ultrasonic signal after it propagates through the member and for producing a received electronic signal representative of the ultrasonic signal received by the receiver.

The apparatus further includes signal conditioning means in communication with the receiver for conditioning the received electronic signal into a conditioned electronic waveform. Comparing means are provided, coupled to the signal conditioning means, for permitting comparison of selected characteristics of the conditioned electronic waveform with known selected characteristics of a canonical waveform. The canonical waveform is obtained due to the interaction of the member with the launched ultrasonic signal as the launched ultrasonic signal propagates at least along the desired path through the member. The comparing means permits comparison of the selected characteristics of the conditioned electronic waveform with the known selected characteristics of the canonical waveform.

An apparatus in accordance with the present invention further includes computing means, responsive to the comparing means, for measuring a propagation time for the desired ultrasonic signal through the member as the time elapsed between the launching of the ultrasonic signal and the receiving of the component of the received ultrasonic signal that propagates through the member along the desired path. The computing means also computes a value for the apparent velocity of the component of the received ultrasonic signal that propagates through the member along the desired path by dividing a determined distance between the receiver and the transmitter by the measured propagation time. The apparent velocity is related to the strength of the member.

BRIEF DESCRIPTION OF THE DRAWINGS

The accompanying drawings, which are incorporated in and constitute a part of this specification, illustrate one embodiment of the invention and, together with the description, serve to explain the principles of the invention.

DESCRIPTION OF THE PREFERRED EMBODIMENT

Figure 1:
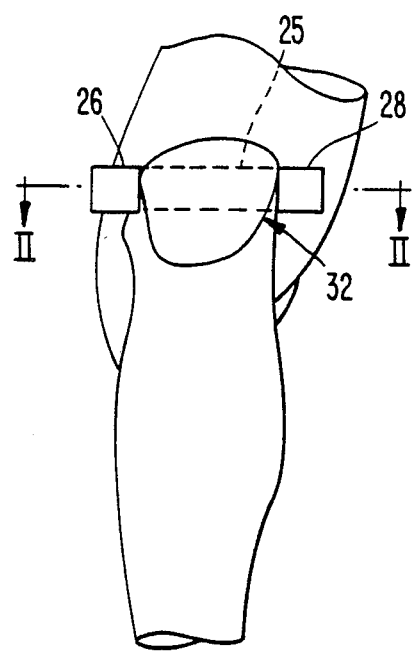
FIG. 1 is a perspective view of a human knee including an ultrasonic transmitter and an ultrasonic receiver positioned proximate a human knee.

Reference will now be made in detail to the present preferred embodiment of the invention, an example of which is illustrated in the accompanying drawings.

A. Bone Construction and Ultrasonic Propagation

To appreciate the present invention, a deeper understanding of the construction of bone, not adequately considered in past ultrasonic measurement techniques, is essential. All bones are composed of the same constituents of crystallized calcium (hydroxyapatite) and organic materials, 90% of which are collagen. The orientation of individual trabecula appears to follow Wolff's Law, a hypothesis relating a bone's structure to its function: the form or shape of bone being given, the bone elements place or displace themselves in the direction of functional stress. The orientation of trabeculae in cancellous bone such as in the femoral neck or in the patellae clearly illustrate this.

With its complex architecture and structural constituents, bone is an anisotropic, inhomogenous, and fluid-filled porous material. "Anisotropic" refers to the differences in mechanical properties (including sound wave velocity) in one direction from those in other directions within the same region of a bone. "Inhomogeneous" refers to the different mechanical properties (such as velocity) in one region of the bone from those in other regions.

As a result, the architecture of a bone is as complex as the forces it must withstand. This has two effects. First, the density and architecture of the bone varies spatially throughout, often in a complex pattern which varies from individual to individual. This accounts for the inhomogeneity of almost all bone. Second, the predominant orientation of the bone matrix is directed along the lines of the predominant forces loading the bone. This imparts anisotropy to the mechanical properties of the bone. A bone, such as the vertebral body which experiences predominantly vertical compression forces, would exhibit much lower strength in the lateral direction.

The velocity of sound reflects the inhomogeneity of the bone through which it propagates. This can be demonstrated, for example, in the human patella where the velocity is a function of the path taken by an ultrasonic signal. Similarly, the velocity of an ultrasonic signal through bone will exhibit anisotropy commensurate with the anisotropy of the bone itself. This is manifest as a large dependence of the velocity on the angle of the propagation path relative to the predominant orientation of the bone matrix.

Inhomogeneity and anisotropy have a significant impact on the measurement of velocity in tissue and require tight control over the protocol to align a measurement probe with a member to be measured. For example, when taking several velocity measurements on an individual, a probe used to launch and receive ultrasonic signals must be accurately repositioned each time to ensure that the acoustic beam traverses the same volume of the bone in the same direction relative to the predominant orientation of the matrix.

Meaningful comparisons of measurements between different individuals requires even tighter controls. The composition and orientation of the matrix of the bone being measured from one individual to the next must be comparable. Given the biological variability between individuals, a carefully designed probe placement protocol is required to place the probe relative to the bone to be measured such that the ultrasonic signal traverses the same path.

Other factors affecting the measurement of velocity include diffraction causing the ultrasonic signal to diverge from the transmitting transducer, refraction within the bone, and internal reflection of the ultrasonic signal when it transverses interfaces within the bone. Further, irregularities in the surface of the bone cause the ultrasonic signal to be coupled into the bone in more than one mode. This is important because bone supports multiple ultrasonic propagation modes, such as transverse and longitudinal modes, and each mode has a different characteristic velocity.

To achieve a measurement which is reproducible in a single individual and comparable between different individuals, it is essential to choose a bone measurement site which permits control of inhomogeneity and anisotropy. Such measurement sites in humans are, for example, the os-calcis, the patella and the distal radius. Of the three, the patella has proven to possess the most desirable characteristics for indicating the presence of osteoporosis in the spine. While the description that follows is directed to applying the method and apparatus of the present invention to a human patella, in vivo, it should be understood that the present invention will find application to a variety of members in vivo, including animal bones and human bones other than the human patella.

Figure 2:
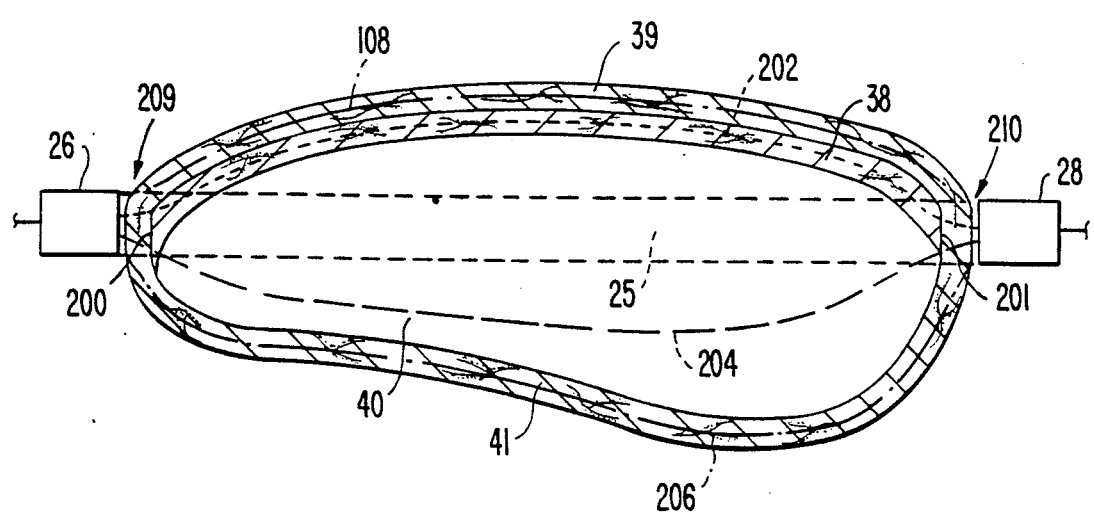
FIG. 2 is a lateral cross-sectional view of a human patella.

The patella is desirable as a bone measurement site for a number of reasons which can be appreciated upon reference to FIGS. 1 and 2. FIG. 1 is a perspective view of a human knee including an ultrasonic transmitter 26 and an ultrasonic receiver 28 positioned proximate the knee, and FIG. 2 is a lateral cross-sectional view of a human patella, in vivo, taken along sectional line II—II of FIG. 1. A first desirable characteristic of the patella is that the medial-lateral aspect of the patella near its anterior surface has nearly parallel surfaces 200 and 201 on its sides which provide surfaces for locating ultrasonic transducers 26 and 28, respectively, to establish an ultrasonic path through the patella. Second, the layer of the soft tissue covering the patella in most individuals, such as the soft tissue layers 209 and 210 separating the transducers 26 and 28, respectively, from the bone are acceptably thin relative to the width of the bone. Third, the desired path taken by an ultrasonic signal through the patella, in vivo, has been determined to be approximately straight, not bent or curved as it can be in some paths through an inhomogeneous, anisotropic solid such as bone.

A desired ultrasonic propagation path through the patella is, for example, located below the denser anterior cortex of the patella in the upper-central portion. This desired ultrasonic propagation path is referred to herein as the "desired path" and is designated in FIG. 2 by the numeral 25. Desired path 25 is, for example, through a region composed predominantly of vertically directed trabeculae. The trabeculae along the desired path presumably developed in this vertically directed orientation in response to primarily compressive forces in this region in accordance with Wolff's law. This upper-central portion of the patella, along which the desired path is located, serves as a desirable diagnostic location because its structure is presumed to be analogous to that in the central portion of the vertebral bodies. Thus, by determining the condition of bone along the desired path through the patella, the condition of bone in the central portion of vertebral bodies can be inferred. It should be understood that alternate desired paths, other than the desired path described above, may be identified through the patella. Such alternate desired paths through the patella and desired paths through members other than a patella are considered to be within the scope of the present invention.

As discussed previously, an ultrasonic signal couples into a human patella, in vivo, in a variety of modes, and therefore takes a variety of paths through the member from transmitter 26 to receiver 28. For example, an ultrasonic signal coupled into a patella at transmitter 26, may propagate along path 202 (shown by dotted lines) through the anterior cortex 38, along path 204 (shown by dashed lines) through the posterior portion 40 of the patella, along path 206 (shown by alternating dot-dash lines) through the posterior soft tissue 41 located posterior to the patella, or along path 208 through the anterior soft tissue 39 located anterior to the patella. In any case, it can be understood that every ultrasonic path traverses at least some soft tissue because soft tissue surrounds the bone.

An ultrasonic signal transmitted by transmitter 26 which propagates through a member 32, such as a patella, in vivo, and is received by receiver 28, includes a plurality of components, each one corresponding to a different path taken by the ultrasonic signal through soft tissue or through both soft tissue and one or more paths through bone. One of the components corresponds to the desired path 25 and is called the "desired signal" or the "diagnostic signal." It is an object of the present invention to ensure that the desired signal is present in the received ultrasonic signal that is received by receiver 28. Once the desired signal is present, one may identify its time of arrival, determine its propagation time and velocity, and relate its velocity to the strength of that portion of the member that lies along the desired path.

Figure 3:
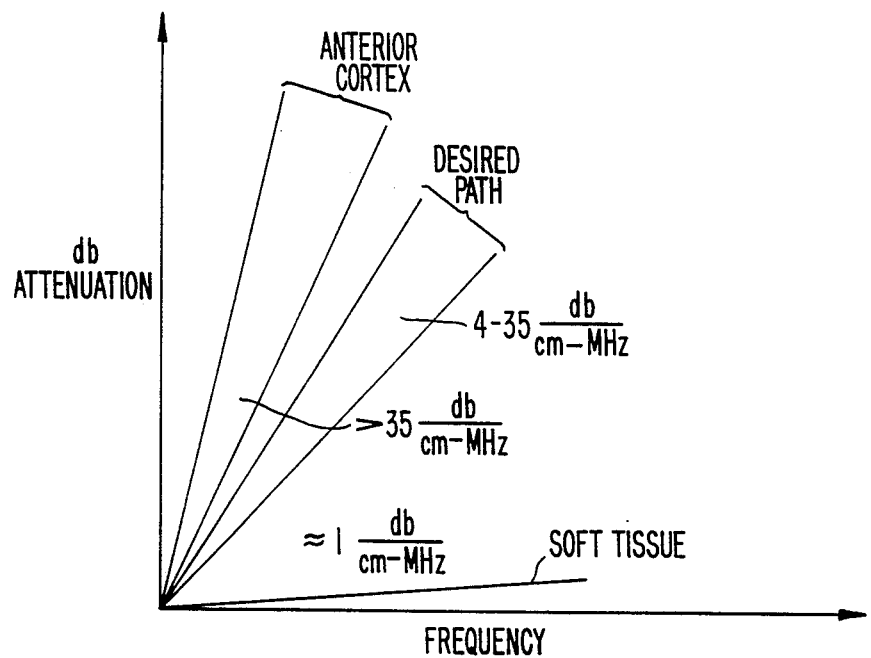
FIG. 3 is a graph of the attenuation of an ultrasonic signal as it propagates through different portions of a human patella.

Each of the different paths through patella lie along different portions of the patella. Each of these portions has differing density and architecture. These different portions of the patella attenuate different frequencies of the transmitted ultrasonic signal spectrum to different degrees. Stated differently, the transmitted ultrasonic signal is a broadband signal and each path through the bone acts as a low-pass filter that allows only a part of the ultrasonic spectrum to pass. This phenomenon is illustrated by the graph shown in FIG. 3.

The ultrasonic signal passing through the anterior cortex 38 shows high attenuation (greater than 35 db/cm-MHz) at high frequencies. The component of the ultrasonic signal propagating along the desired path produces an intermediate amount of attenuation (4–35 db/cm-MHz). The component of the ultrasonic signal propagating through soft tissue, such as found in the posterior soft tissue 39 or the anterior soft tissue 41, shows comparatively less attenuation (approximately 1 db/cm-MHz) at any of the frequencies transmitted into the patella.

It has been found that the velocity of an ultrasonic signal through dense bone, such as found in the anterior cortex, is higher than that through less dense bone, such as the bone traversed by the desired path. The velocity of an ultrasonic signal is still lower through soft tissue. Thus, the component of a received signal attributable to propagation through dense bone arrives first, followed by a component that propagates through less dense bone along the desired path, followed by a component that propagates through soft tissue. While the transmitted ultrasonic signal does take a pluarality of paths, the intensity of the ultrasonic signal diminishes at paths located radially outwardly from the direct path established between transmitter 26 and receiver 28. For example, the intensity of the ultrasonic signal that propagates along a path through posterior soft tissue 39 or anterior soft tissue 41 is less than that which propagates along desired path 25 between transmitter 26 and receiver 28.

Figure 4A:
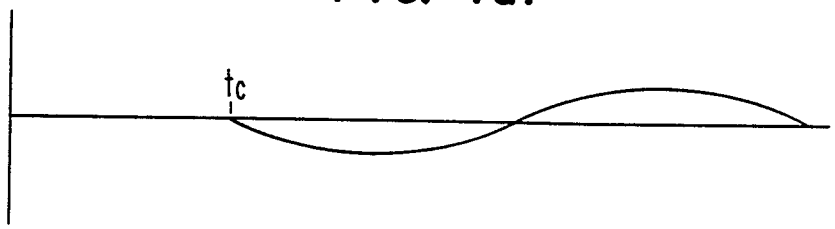
FIG. 4a is a graphical representation of the component of an ultrasonic signal that propagates through the anterior cortex of the human patella.
Figure 4B:
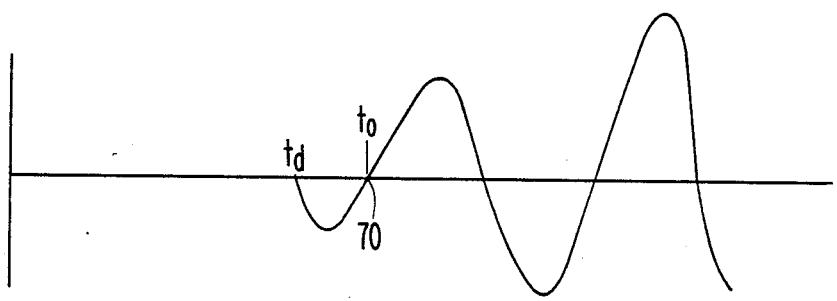
FIG. 4b is a graphical representation of the component of an ultrasonic signal that propagates through the desired path in a human patella.
Figure 4C:
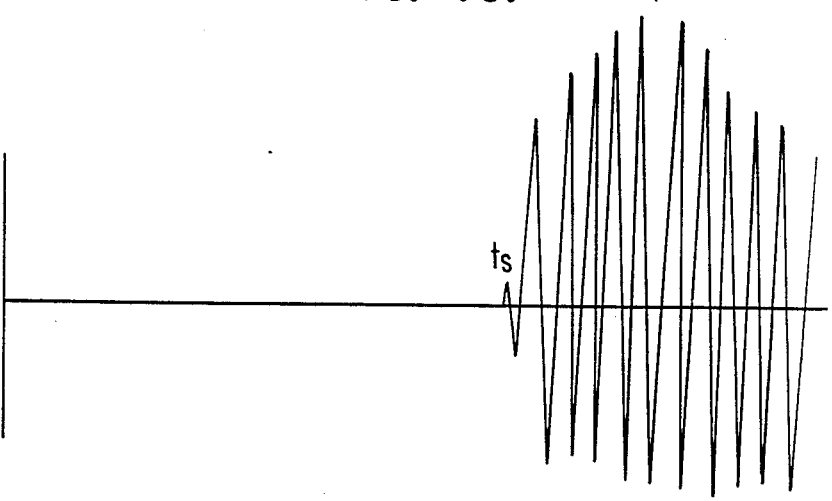
FIG. 4c is a graphical representation of the component of an ultrasonic signal that propagates through the soft tissue surrounding a human patella.

FIGS. 4a–4c represent the components of the received waveform that propagate along different paths. FIG. 4a shows the waveform of the component of the received wave that has propagated through the anterior cortex 38 along path 202, the time of arrival of which is $t_c$. FIG. 4b shows the waveform of the component of the received wave that has propagated along desired path 25, the time of arrival of which is $t_d$, and is a waveform representation of the "desired signal." FIG. 4c shows a waveform of the component of the received wave that has propagated through overlying soft tissue 39 or 41, along path 208 or 206, respectively, the time of arrival of which is $t_s$.

Figure 4D:
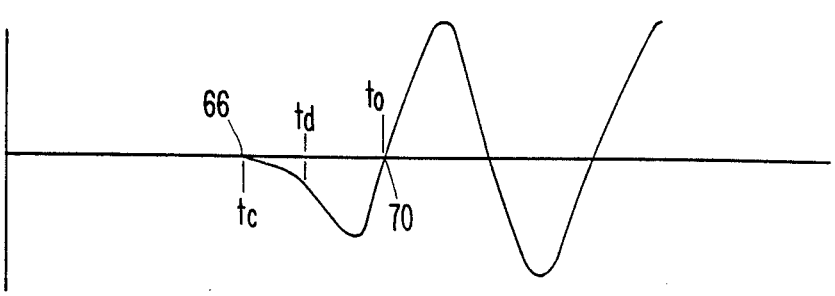
FIG. 4d is a graphical representation of the an ultrasonic signal which propagates through both the anterior cortex and through the desired path in a human patella.

FIG. 4d shows a complex waveform that includes the components of FIGS. 4a and 4b. For the sake of simplicity, the component of the received wave that propagates through the soft tissue has been omitted from FIG. 4d. As shown in FIG. 4d, breakpoint 66 is the point at which ultrasonic energy is first received by receiver 28. Breakpoint 66 occurs at time $t_c$ when the component of the ultrasonic signal that traverses anterior cortex 38 is received. This component has a lower frequency and amplitude and a higher velocity, and arrives before the other components. Thus, to gauge the time of arrival of the desired signal, $t_d$, accurately, that time of arrival must be differentiated from the time of arrival of the component that propagates through the anterior cortex, $t_c$. The method and apparatus in accordance with the present invention for accomplishing this differentiation is more fully described below.

B. A Canonical Waveform

Figure 5:
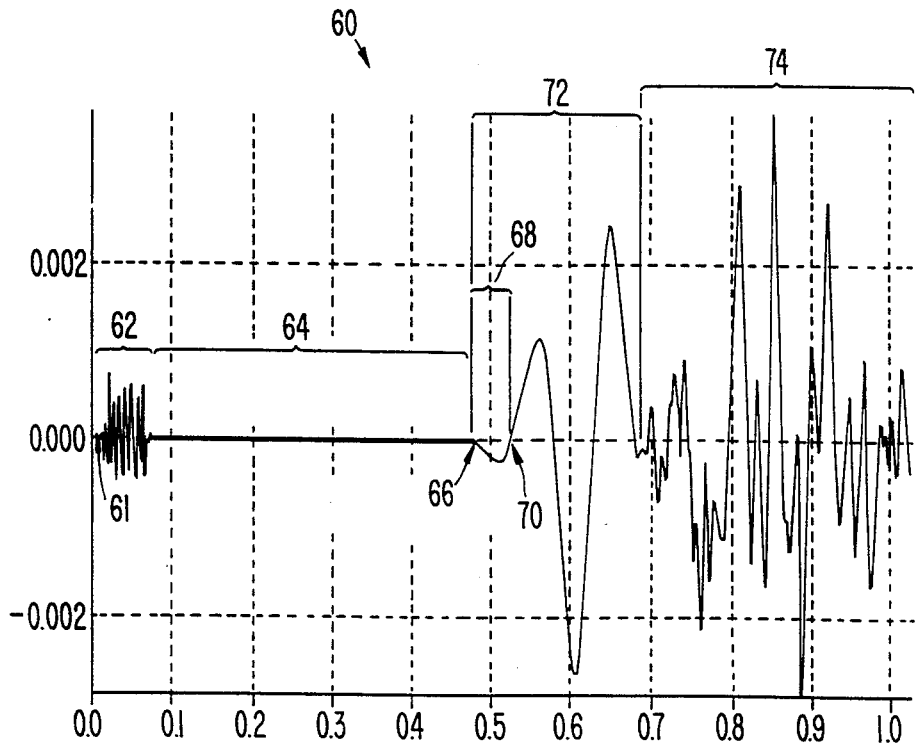
FIG. 5 is a depiction of a canonical waveform used in accordance with the present invention.

FIG. 5 shows a conditioned electronic waveform referred to as a "canonical waveform" and is designated, generally, by the numeral 60. The term "canonical" designates a generic waveform that is produced whenever the transmitted ultrasonic signal propagates at least along desired path 25, is received by receiver 28, which produces a received electronic signal that is then conditioned by signal conditioning electronics.

Canonical waveform 60 shown in FIG. 5 is for the purpose of illustration only and it may vary significantly in appearance, amplitude or relative energy distribution between the bone and soft tissue components and should not be construed as limiting the present invention. Further, canonical waveform 60 may vary when generated for members other than a human patella such as animal bones and human bones other than a human patella.

Much of the complexity of canonical waveform 60 is the result of many different components of the transmitted ultrasonic signal propagating along different paths and arriving at the receiver at different times. An important feature of canonical waveform 60 is that the first arriving component of the conditioned waveform is associated with the component of the transmitted ultrasonic signal that propagates along the desired path 25 and that the arrival time of that component can easily be determined.

Canonical waveform 60 includes several characteristics such as a leader 61 an initial impulse 62, a baseline 64, a baseline break 66, a first deviation 68, a first zero amplitude point 70, a bone signal 72 and a soft tissue signal 74. Canonical waveform 60 may also be characterized in the amount of energy contained in bone signal 72 and soft tissue signal 74, both in absolute and in relative terms. That is, the bone signal 72 has a certain amount of energy associated with it and tissue signal 74 has a certain amount of energy associated with it.

Leader 61 is a short stretch of samples that are collected before the ultrasonic excitation is transmitted. Initial impulse 62 is a burst of electromagnetic interference, or "crosstalk," that is detected by signal processing electronics, more fully discussed below, when the ultrasonic signal is transmitted. Initial impulse 62 does not represent any ultrasonic signal present at receiver 28 but is useful to verify the time at which the ultrasonic excitation is transmitted. If canonical waveform 60 is displayed on a video display device, the horizontal scale and offset of the waveform display may be adjusted to eliminate the depiction of initial impulse 62.

Baseline 64 occurs after the initial impulse dies away and before the transmitted acoustical signal arrives at receiver 28. Baseline 64 is the zero amplitude component of the waveform used to establish noise thresholds that are used to detect the arriving acoustical energy. Baseline break 66 is the point at which ultrasonic energy is first received by receiver 28.

First deviation 68 is the first excursion of canonical waveform 60 from baseline 64. FIG. 5 shows first deviation 68 as being a negative half-cycle. Preferably, the ultrasonic signal as transmitted by transmitter 26 has a first half-cycle of a first polarity and canonical waveform 60 has a first half-cycle of the first polarity. It has been found that by ensuring the same polarity for the first half-cycles of the the canonical waveform and the transmitted ultrasonic signal, one can have a great deal of confidence that the transmitted ultrasonic signal represented by canonical waveform 60 propagated along the desired path and was neither refractively bent nor subject to excessive phase cancellation at the receiving transducer. The term "phase cancellation" refers to a condition where an ultrasonic signal propagates along two or more different paths which arrive at a receiver out of phase such that they cancel each other. The first zero amplitude point 70 marks the end of first deviation 68 and is the first point after the baseline break 66 at which the received waveform has an amplitude of zero.

Figure 6:
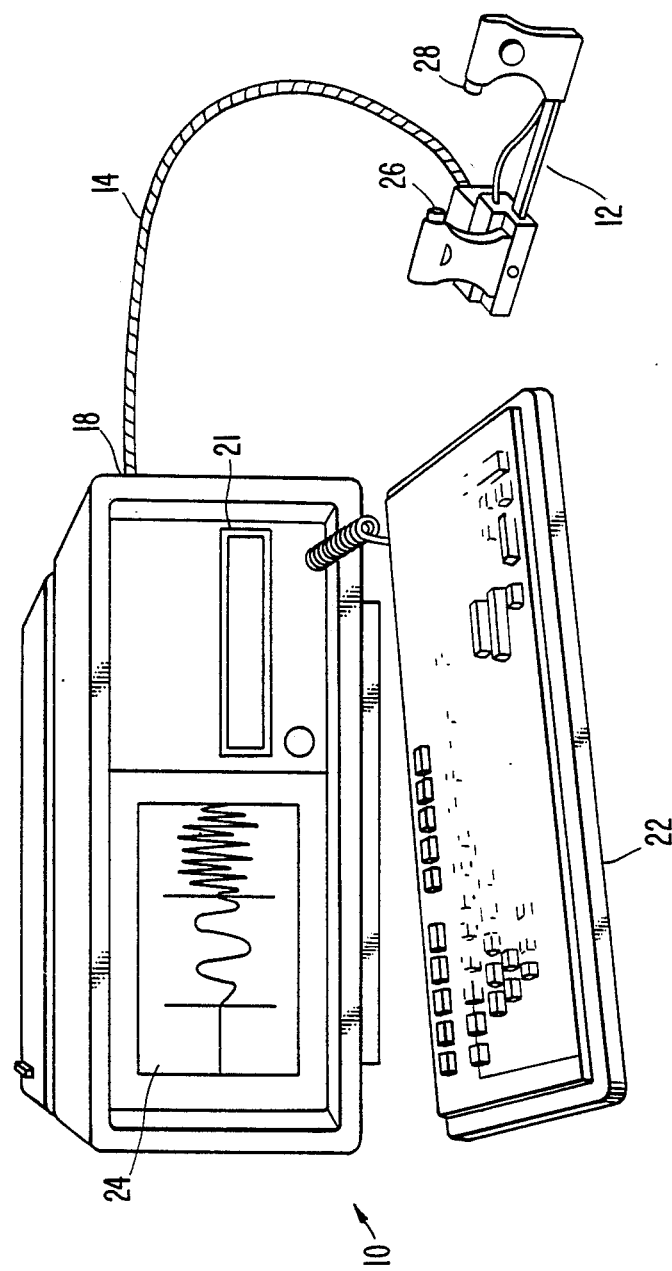
FIG. 6 is a perspective view of an apparatus for the ultrasonic analysis of a member in accordance with the present invention.

C. Method and Apparatus for Directing an Ultrasonic Signal Along Desired Paths and for Determining Strength of Members In accordance with the present invention, a method is provided for directing an ultrasonic signal along a desired ultrasonic path through a member and for establishing the strength of the member. The ultrasonic signal is capable of propagating along a plurality of ultrasonic paths, the member interacting with ultrasonic signals differently along each of the plurality of paths. An apparatus useful in carrying out the method of the present invention is shown in perspective view in FIG. 6 and in block diagram form in FIG. 7 and is designated generally by the numeral 10. The apparatus includes a probe 12 that is in communication with a computer 18 and associated ultrasonic front end 23 through a probe cable 14. Computer 18 includes a central processing unit (hereinafter, "CPU") 19, a video display 24, storage unit 20 (FIG. 7) such as a disk drive 21 (FIG. 6) for storing and reading information about a member being examined, and an ultrasonic front end 23 (FIG. 7) for providing an interface between the CPU 19 and the remainder of the ultrasonic system. A keyboard 22 is provided to enter information into computer 18. Such information may include information about a patient, information about measurement parameters to be changed or information concerning the manner in which waveforms are to be displayed on video display 24. The structure and function of these elements is more fully described below.

Figure 8A:
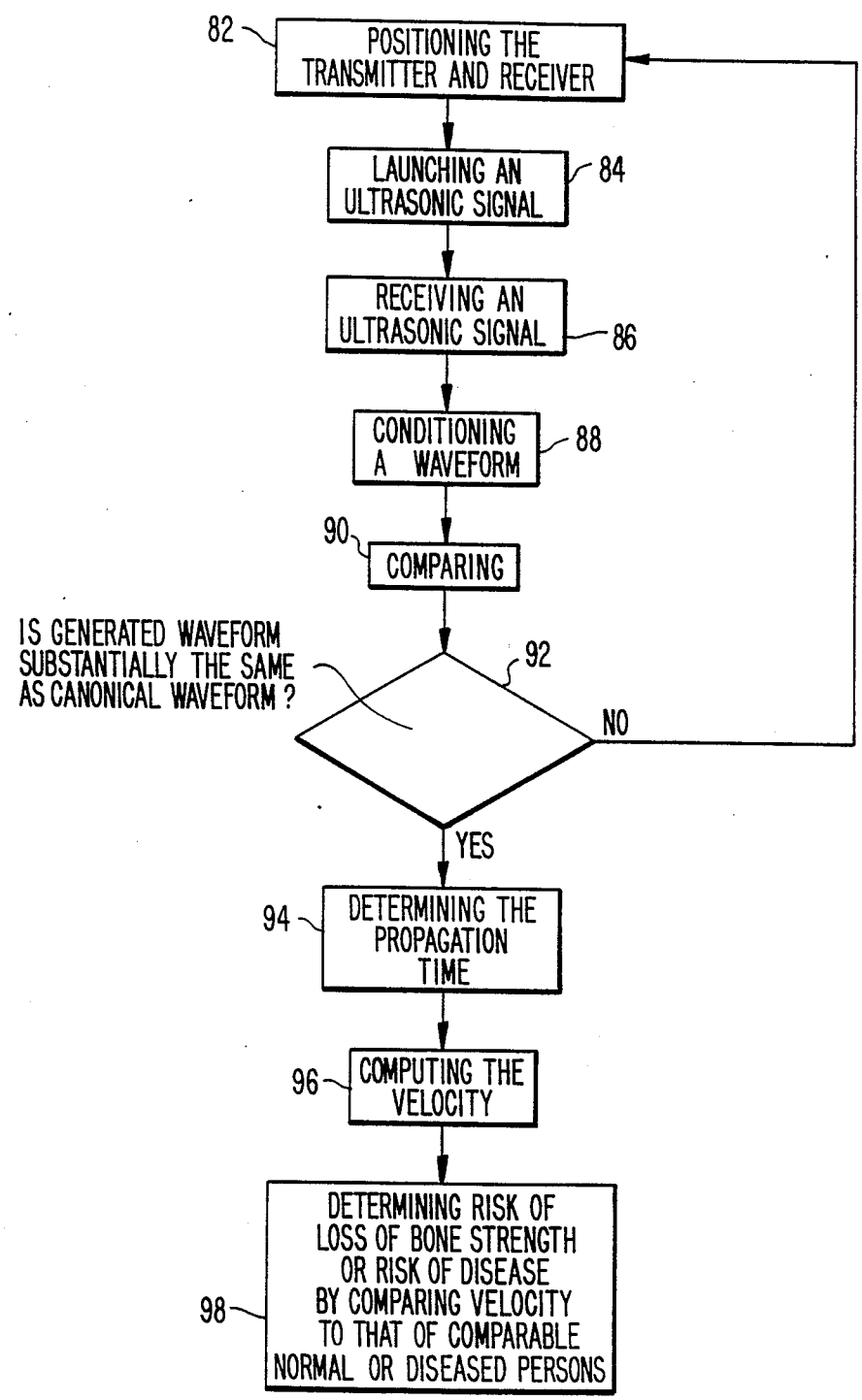
FIG. 8A is a flow chart of a method for directing an ultrasonic signal along a desired path and determining the strength of a member in accordance with the present invention.
Figure 8B:
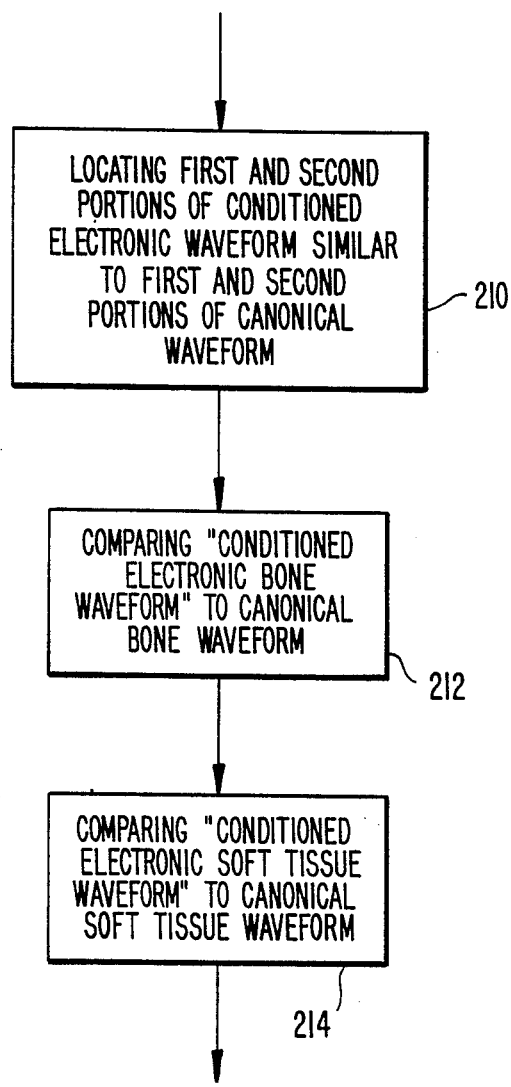
FIG. 8B is a flow chart of a method for comparing a conditioned electronic waveform with a canonical waveform.

FIGS. 8A and 8B show a preferred procedure to implement the method of the present invention. In accordance with the present invention, the method includes the step of positioning an ultrasonic transmitter and an ultrasonic receiver proximate the member to establish a direct ultrasonic path between the transmitter and the receiver approximately along the desired path (step 82).

Figure 7:
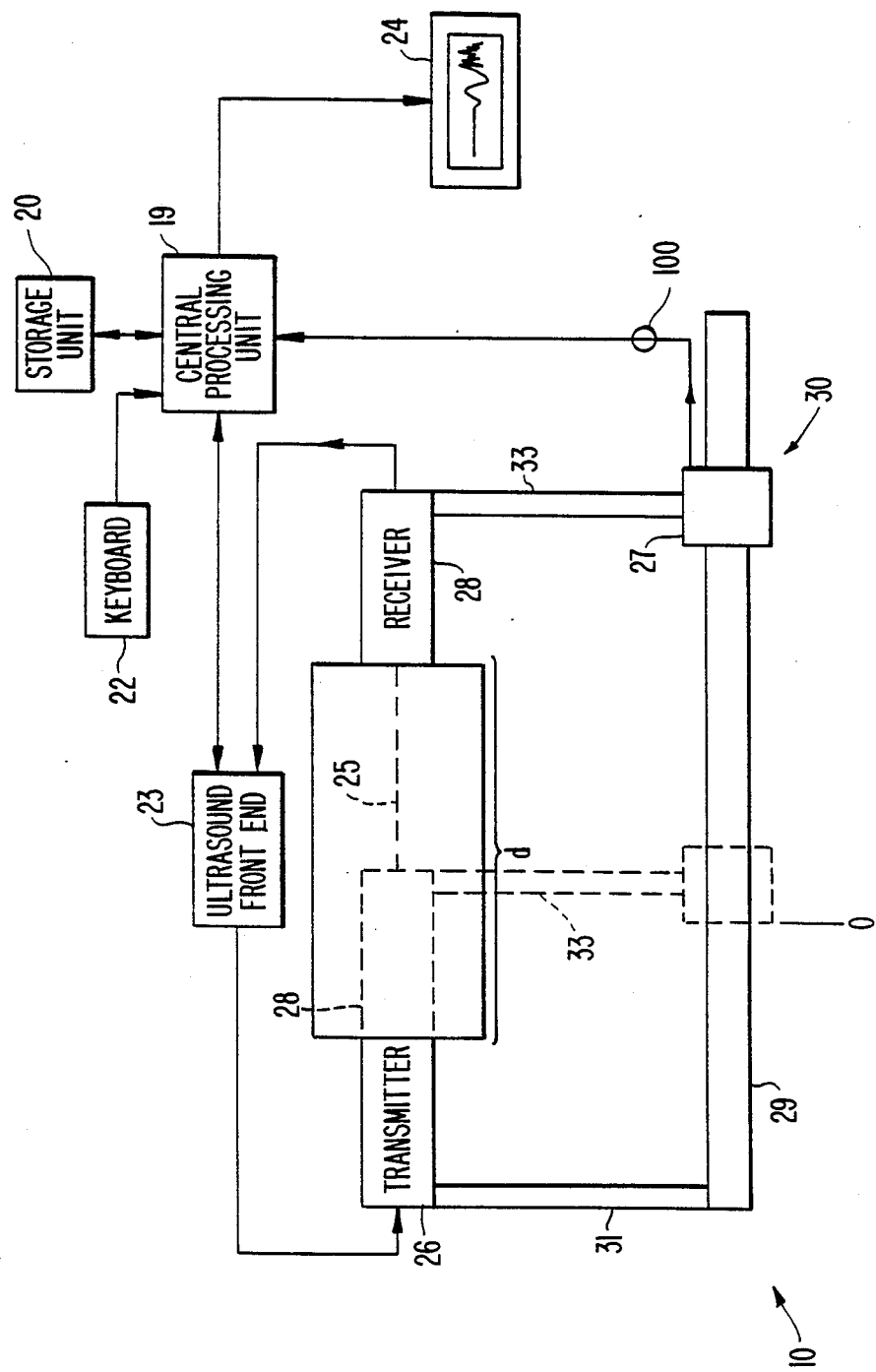
FIG. 7 is a block and schematic diagram of the apparatus of FIG. 1.

An apparatus useful in carrying out the method of the invention includes a probe 12. Probe 12 includes an ultrasonic transducer 26 and ultrasonic transducer 28. As shown in FIGS. 1, 2 and 7, transmitter 26 and receiver 28 are capable of being positioned proximate a member 32, such as a patella, in vivo, such that desired path 25 is established between them. Preferably, the transmitter and the receiver are positioned on either side of the member. Alternatively, the transmitter and the receiver can be positioned on the same sides of the member. In either case, transmitter 26 and receiver 28 must be disposed proximate member 32 so as to establish a direct ultrasonic path along a desired path such as, for example, along desired path 25.

Transmitter 26 and receiver 28 are preferably acoustically coupled to member 32. This can be accomplished by applying an acoustic coupling medium, such as an acoustic coupling gel, not shown, between transmitter 26 and member 32 and between receiver 28 and member 32.

Figure 9:
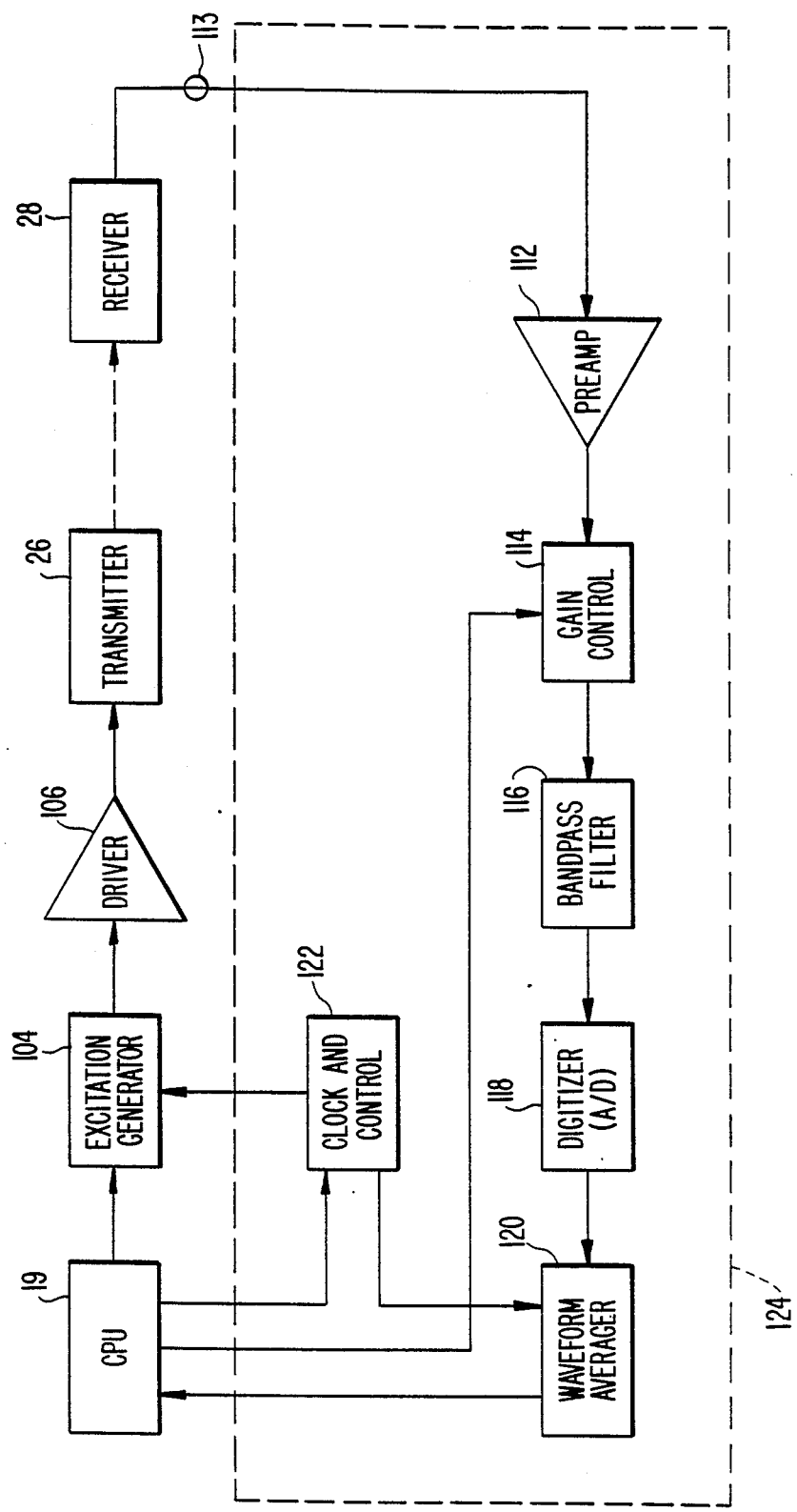
FIG. 9 is a block circuit diagram of an embodiment of waveform generating means in accordance with the present invention including an automatic gain ranger.
Figure 10:
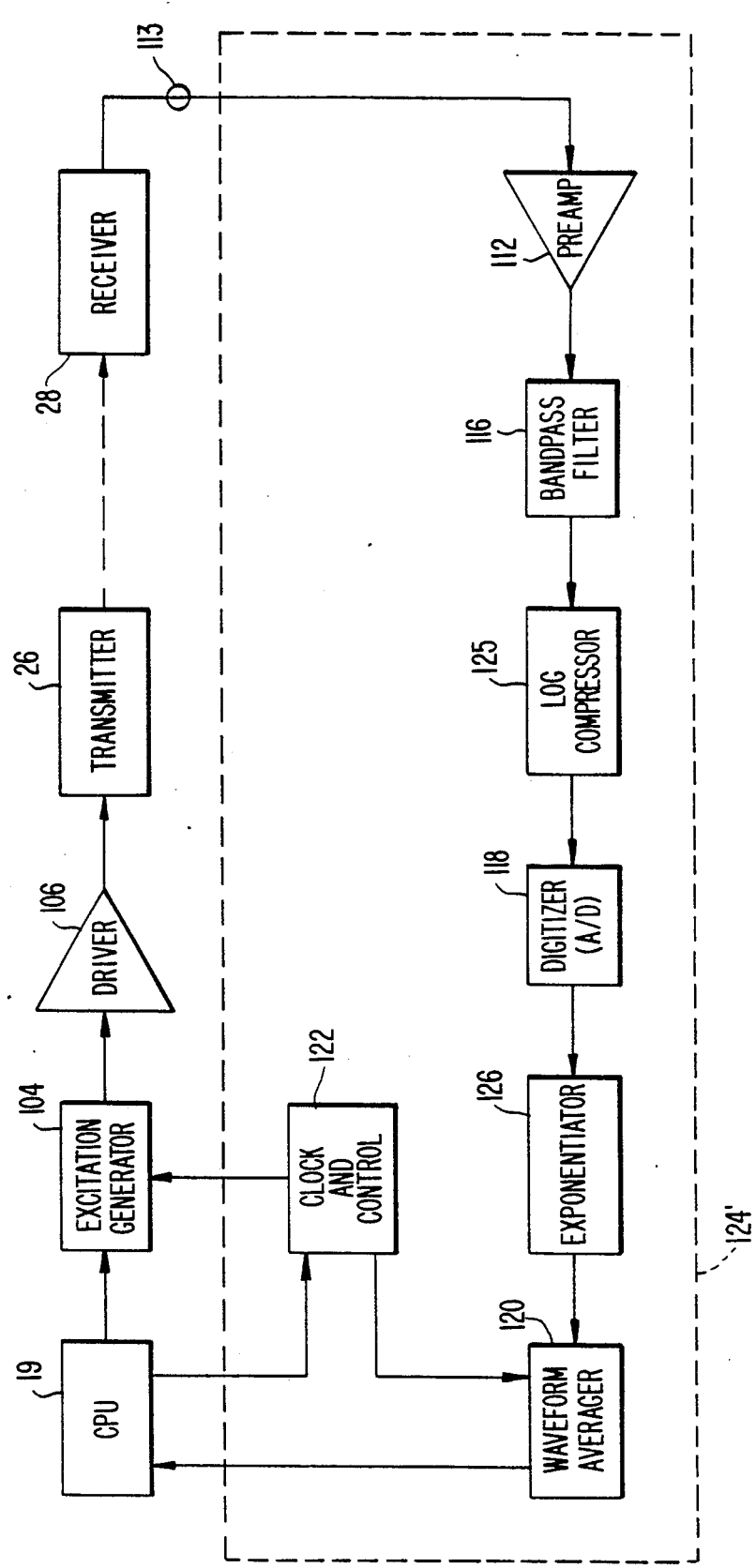
FIG. 10 is a block circuit diagram of an embodiment of waveform generating means in accordance with the present invention including a log compressor.

In accordance with the present invention, the method includes the step of launching an ultrasonic signal into the member toward the receiver (step 84). FIGS. 9 and 10 show alternate embodiments of certain electronic components of apparatus 10. As shown in FIGS. 9 and 10, CPU 19 controls an excitation generator 104 that generates a burst of cycles of a periodic electronic signal. The signal from excitation generator 104 is amplified by driver 106 and converted into ultrasonic signals by transmitter 26. Transmitter 26 is capable of sending an ultrasonic signal through member 32 where it is received by receiver 28. Preferably, transmitter 26 and receiver 28 are identical ultrasonic transducers such as, for example, Model No. V533, manufactured by Panametrics of Waltham, Massachusetts, U.S.A. Such ultrasonic transducers are preferably capable of sending and receiving an ultrasonic signal with a nominal center frequency of 2.25 MHz, with approximately 6 db bandwidth of 80%, and having significant signal energy within the 100-600 KHz band. As discussed, bone attenuates higher frequencies. Thus, by ensuring that the transmitted ultrasonic signal includes significant energy in the 100-600 KHz range, one can be sure that sufficient ultrasonic energy propagates along a path through bone and is detectable by receiver 28. Preferably, the transmitted ultrasonic signal is of a short duration, for example, on the order of 5 microseconds.

In accordance with the present invention, the method includes the steps of (1) receiving the launched ultrasonic signal after it propagates through the member and producing a received electronic signal representative of the ultrasonic signal received by the receiver (step 86) and (2) signal conditioning the received electronic signal to produce a conditioned electronic waveform (step 88).

To carry out the method of the present invention, signal conditioning means are provided that condition a received electronic signal produced by receiver 28 into a conditioned waveform representing the received ultrasonic signal received by receiver 28. In the preferred embodiment, the signal conditioning means includes the components enclosed in dashed boxes 124 and 124' shown in FIGS. 9 and 10.

In these figures, respectively, the received electronic signal from receiver 28 passes along a line 113 and is amplified by a preamplifier 112. As embodied herein, preamplifier 112 provides 100 db of gain, G, (equal to a factor of about 100,000). The amplified signal is then passed through some components described below and becomes an input to digitizer 118 which samples the amplified signal at 20 megasamples per second and digitizes it using an 8-bit analog to digital converter. In this manner, 1024 samples are collected, each sample being called a "point" and a collection of points being called a "record."

In order to improve the signal to noise ratio of the system, thirty-two (32) records are obtained in succession and averaged point-by-point by a waveform averager 120. The resulting collection of 1024 averaged points is called a "conditioned electronic waveform." The conditioned electronic waveform is an electronic representation of the received ultrasonic signal and may be displayed on a video display 24, stored in storage means 20 or further processed by CPU 19.

Clock and control 122 is provided to ensure that processing of received ultrasonic signals occurs in the proper sequence. Signal conditioning means 124 further includes a bandpass filter that allows a band of 20 KHz to 3 MHz to pass.

Preferably, signal conditioning means 124 include automatic gain ranging means to ensure that the amplitude of the received ultrasonic signal is in a preferred range of values. The automatic gain ranging means provides linear operation of signal conditioning means 124. As embodied herein, automatic gain ranging means may be disposed in ultrasonic front end 23 and, as shown in FIG. 9, may include a gain control 114 operably connected to CPU 19. Gain control 114 is capable of 0-60 db of attenuation.

Alternatively to the automatic gain ranging means, signal conditioning means 124 may include log compressing means to log compress the received ultrasonic signal to ensure that the amplitude of the received ultrasonic signal is in a preferred range of values. Thus, the log compressing means provide for the linear operation of the waveform generating means. As shown in FIG. 10, log-compressing means may include a log compressor 125 and an exponentiator 126. Log compressor 125 converts the signal passing through bandpass filter 116 into the logarithm of that signal.

The received electronic signal produced by receiver 128 includes sinusoidal waves which are alternatively positive and negative and pass through zero frequently.

Thus, as is known to those skilled in the art of signal processing, one cannot simply take the logrithm of the received electronic signal. Thus, instead of calculating log(s), where s is the received electronic signal, log compressor 125 calculates clog(s), where $$clog(s) = \begin{cases} -\log(s) \text{ for } s < -L \\ Q^*(s) \text{ for } -L \leq s \leq L \\ \log(s) \text{ for } s > L; \end{cases}$$

L is chosen such that for small amplitudes of s, that is, for $|s| \leq L$, the clog(s) reverts to linear operation. This avoids the log going negative, to minus infinity, or an undefined number as s goes from below one to zero or to a negative value. The value for L is chosen to be greater than one and $Q=\log(L)$ so that the clog operation is a continuous function of s with no discontinuities around the $|s|=L$ transition from log to linear operation.

Exponentiator 126 expands the digitized logarithm of the signal to its original form. The signal is then processed in the manner described in reference to signal conditioning means 124 to produce a conditioned electronic waveform.

In accordance with the present invention, the method includes the step of comparing selected characteristics of the conditioned electronic waveform with corresponding selected characteristics of a canonical waveform (step 90). The canonical waveform is obtained due to the interaction of the member with the launched ultrasonic signal as the launched ultrasonic signal propagates at least along the desired path through the member.

To carry out the method of the present invention, comparing means includes CPU 19. As discussed above, the conditioned electronic waveform is the output from the waveform averager 120 and is in the form of a digital representation of an electrical signal. This digital representation can be sampled to provide selected characteristics about the conditioned electronic waveform. Similarly, selected characteristics of canonical waveform 60 are represented digitally and stored in CPU 19. The selected characteristics of canonical waveform 60 may, Therefore, be electronically compared with the selected characteristics of the conditioned electronic waveform in CPU 19.

Alternatively, the conditioned electronic waveform may be displayed on video display 24 where the operator can visually compare the conditioned electronic waveform with a visual representation of canonical waveform 60 or compare the conditioned electronic waveform with canonical waveform 60 known to the operator. Computer 18 may, therefore, include displaying means for displaying a conditioned electronic waveform such as a video display 24. A conditioned electronic waveform is shown displayed on video display 24 for the purpose of illustration only and should not be construed as representing a waveform in accordance with the present invention or limiting the present invention in any way.

Preferably, CPU 19 compares canonical waveform 60 with the conditioned electronic waveform to determine whether the conditioned electronic waveform has substantially the same characteristics as canonical waveform 60. A preferred procedure for such automatic comparision is shown in FIG. 8B. Since the canonical waveform has characteristics indicative of an ultrasonic signal that has propagated along the desired path through the member, one can conclude that the received ultrasonic signal has propagated along the desired path when the conditioned electronic has substantially the same characteristics as the canonical waveform.

Preferably, this would occur when the conditioned electronic waveform and the canonical waveform include a first portion and a second portion, the first portion of the canonical waveform and the conditioned electronic waveform corresponding to the transmitted ultrasonic signal that propagates along a path through the bone and the second portion of the canonical waveform and the conditioned electronic waveform corresponding to the transmitted ultrasonic signal that propagates along paths including at least paths through the bone and through the soft tissue.

As shown in FIG. 5, canonical waveform 60 includes a first portion which is a bone signal 72 and a second portion which is a soft tissue signal 74. Bone signal 72 includes components representative of the transmitted ultrasonic waveform that propagated through the patella such as through the desired path 25 and possibly through the anterior cortex 38 as well. Soft tissue signal 74 is a composite waveform that includes components representative of the transmitted ultrasonic signal that propagated through both the patella and through the soft tissue surrounding the patella.

Preferably, CPU 19 effects the waveform comparison by first locating first and second portions of the conditioned electronic waveform which are similar to first and second portions of the canonical waveform (step 210). CPU 19 then compares the first portion of the conditioned electronic waveform, called the "conditioned electronic bone waveform" to the bone signal of canonical waveform 60 called the "canonical bone waveform" (step 212). CPU 19 compares the second portion of the conditioned electronic waveform, called the "conditioned electronic soft tissue waveform," to tissue signal of canonical waveform 60 called the "canonical soft tissue waveform" (step 24). These substeps to the comparing step 90 of FIG. 8A are shown in flow chart form in FIG. 8B.

Preferably, the principal frequency of the canonical waveform during the first portion falls in a first frequency range and the principal frequency of the canonical waveform during the second portion falls in a second frequency range which is different from the first frequency range. As shown in FIG. 5, the bone signal 72, which corresponds to the first portion, has a much different frequency than does the soft tissue signal 74, which corresponds to a second portion. This reflects the fact, as explained in reference to FIG. 3, that the soft tissue barely attenuates a frequency range in the spectrum transmitted by transmitter 26, whereas bone located along the desired path attenuates higher frequency signals more severely. Thus, the bone signal and the soft tissue signal can be distinguished by their different principal frequencies.

As embodied herein, and shown in FIG. 8, the method includes the step of determining whether the conditioned electronic waveform is substantially the same as the canonical waveform (step 90). Preferably, a predetermined part of the first frequency range of the first portion of the conditioned electronic waveform contains energy of a first desired amount and a predetermined part of the second frequency range of the second portion of the conditioned electronic waveform contains energy of a second desired amount. As the transmitter 26 and the receiver 28 are simultaneously moved in the anterior direction relative to the patella proportionally more of the transmitted ultrasonic signal propagates through the soft tissue that covers the anterior portion of the patella. Similarly, as the transmitter 26 and the receiver 28 are moved in the posterior direction relative to the patella, proportionally more of the signal propagates through the patella bone itself. The relative amount of energy represented by the bone and the tissue signals is, therefore, an indicator of the position of the transmitter 26 and the receiver 28 relative to the patella. This relative energy can be computed in the following manner.

A 512 point waveform is created from digitized points 512 through 1023 of the conditioned electronic waveform and is called a "check wave." The check wave is "windowed" by measuring the waveform amplified with trapezoidal window that rises linearly from zero to one over the first 25 points of the check wave, remains constant for the next 462 points, and then falls from one to zero over the last 25 points of the check wave.

After windowing, CPU 19 computes a Fourier transform of the check wave to obtain the magnitudes of the "windowed" check wave as a function of frequency ranges. Three integrals of the magnitude function are then computed by CPU 19 as follows:
LFE=integral from 19.5 KHz to 0.5 MHz;
HFE=integral from 0.5 MHz to 3.5 MHz; and
TOT=integral from 19.5 KHz to 10 MHz.

LFE is the integral of the low frequency component of the check wave and is related to the energy in the bone signal 72 and HFE is the integral of the high frequency component of the check wave and is related to the energy in the soft tissue signal 74. TOT is related to the total energy in the check wave. For a conditioned electronic waveform produced when an ultrasonic signal propagates along desired path 25, the following two conditions are met:

1. LFE/TOT>0.15; and
2. HFE/TOT>0.40

If the first condition is not met, the conditioned electronic waveform has a bone signal that is too low and the conditioned electronic waveform is rejected as not being equivalent to canonical waveform 60. This condition would obtain if the transmitter 26 and receiver 28 were too posterior or too anterior of the desired path 25. If the second condition is not met, the conditioned electronic waveform has a tissue signal that is too low and the conditioned electronic waveform is rejected as not being equivalent to canonical waveform 60. This condition would obtain if the transmitter 26 and the receiver were located posterior to the desired path, but not so far posterior so as to generate a low bone signal.

During the positioning of the transmitter and receiver proximate the member, a number of waveforms may be generated that do not have substantially the same characteristics as the canonical waveform. Examples of such conditioned electronic waveforms are illustrated in FIGS. 11-13.

Figure 11:
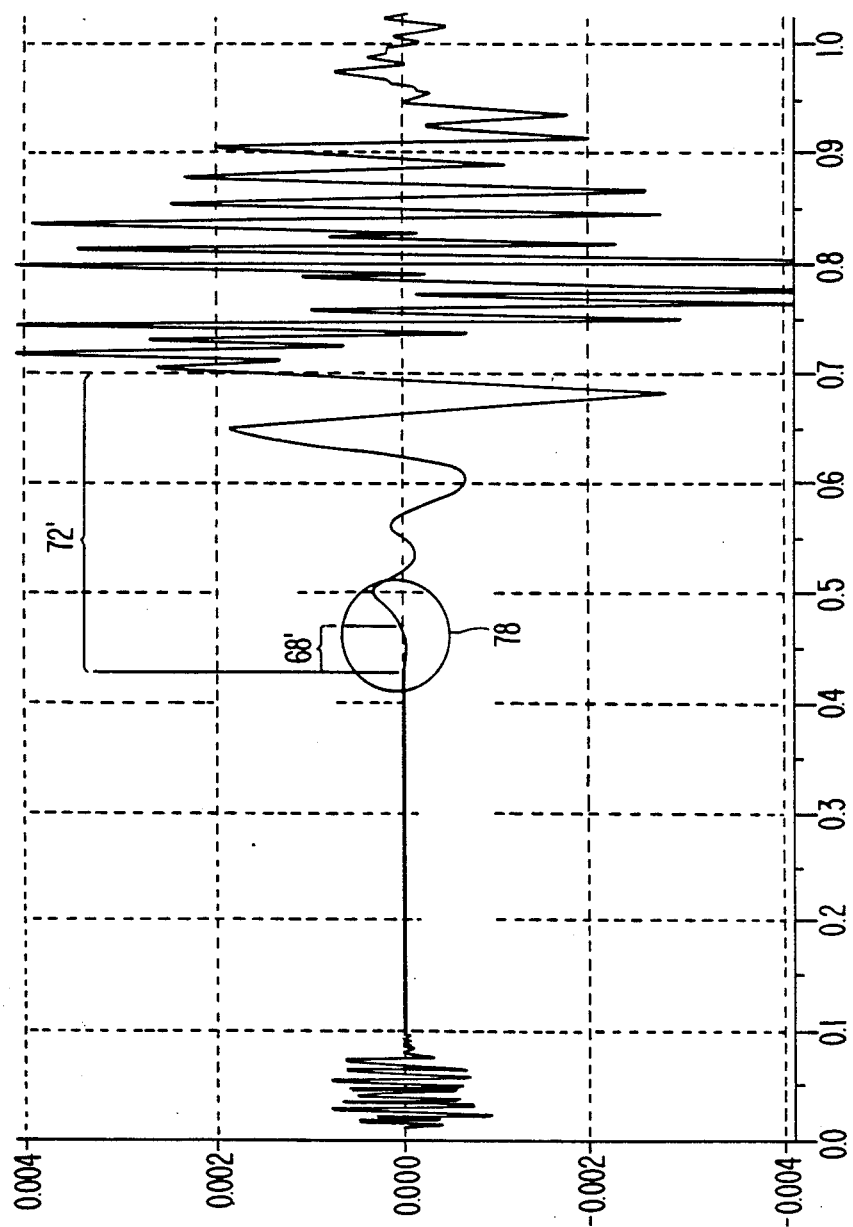
FIGS. 11-13 are representations of received ultrasonic waveforms that have passed through a human patella along different paths from the desired path through the patella in accordance with the present invention.

FIG. 11 shows a conditioned electronic waveform in which the amplitude of the initial part 78 of the conditioned electronic bone signal is too small and in which a first deviation 68' of a bone signal 72' is characteristic of a conditioned electronic waveform that is not a canonical waveform. This type of a conditioned electronic waveform can result from several causes such as refractive bending of the ultrasonic signal or an insufficient fraction of the ultrasonic signal propagating along the desired path. The waveform of FIG. 11 can also result from phase cancellation of the receiving transducer. See Klepper, et al., "Application of Phase-Insensitive Detection and Frequency Dependent Measurements to Computed Ultrasonic Attenuation Tomography," IEEE Trans, Biomedical Engineering, Vol. BME-28, No. 2, Feb. 1981.

Figure 12:
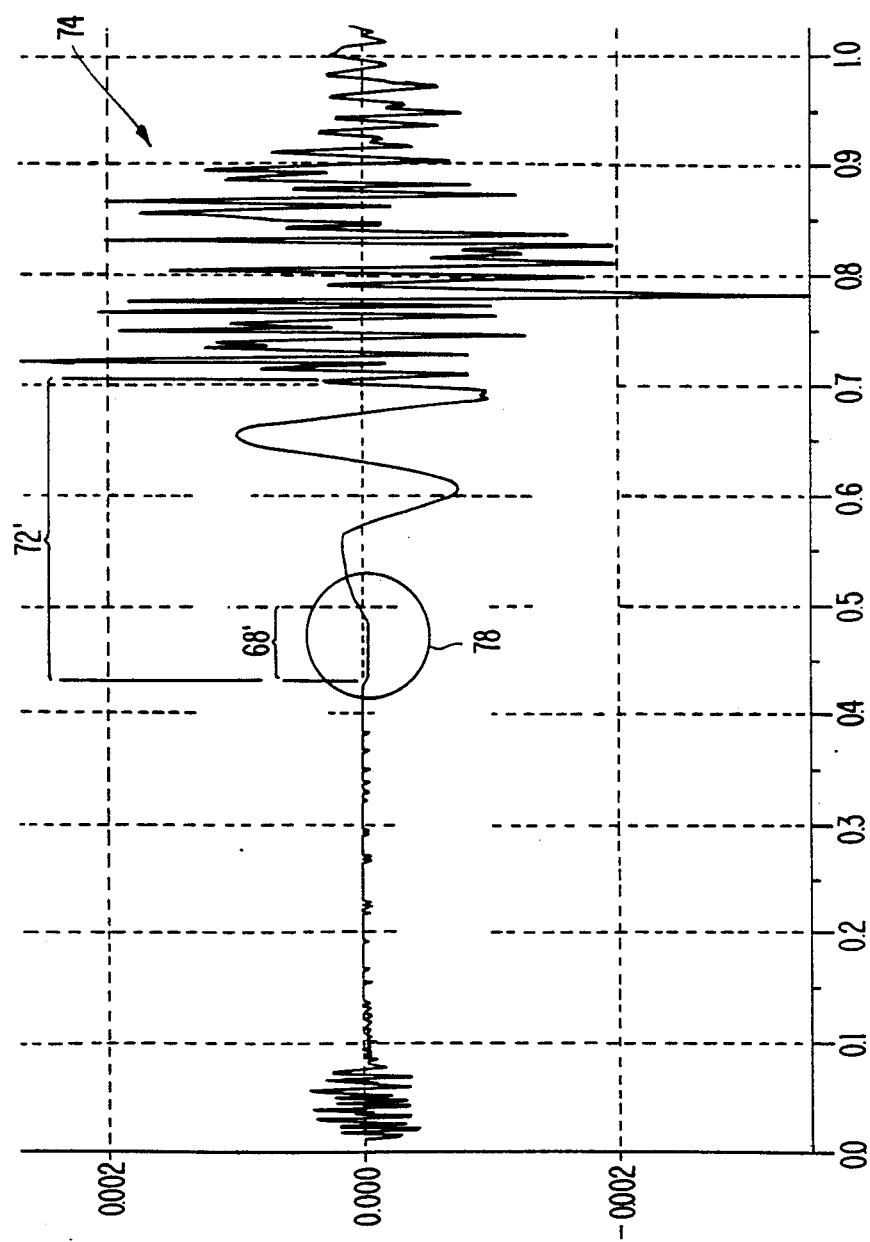

FIG. 12 also shows a conditioned electronic waveform in which the first part of the conditioned electronic bone signal has too small an amplitude and in which a first deviation 68' of a bone signal 72' is characteristic of a conditioned electronic waveform that is not a canonical waveform. The reasons for the conditioned electronic waveform of FIG. 12 may be the same as given for the waveform of FIG. 11.

Figure 13:
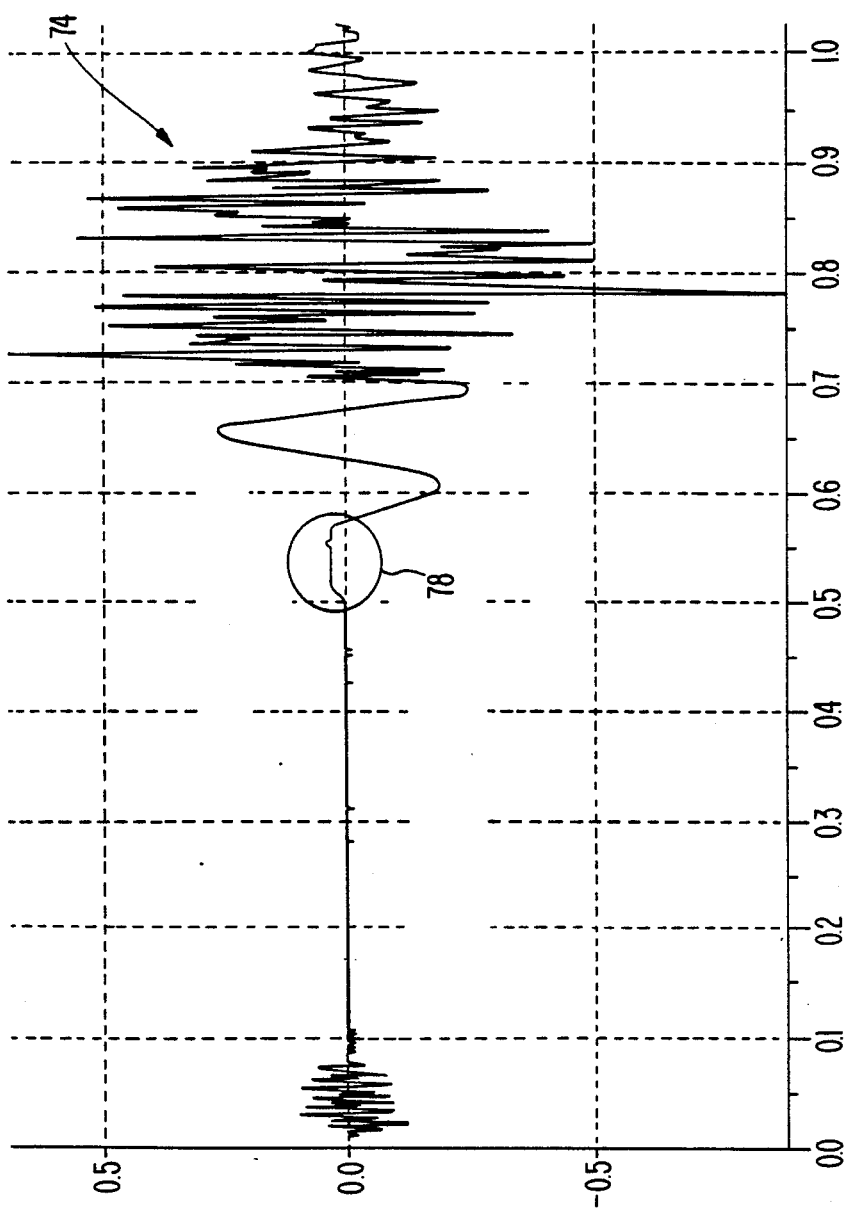

FIG. 13 shows a conditioned electronic waveform in which the first deviation of the conditioned electronic bone signal is missing altogether and the amplitude of the initial bone signal is too small. This can result from the reasons cited above in relation to FIG. 11. These reasons result in a condition wherein an unreliable first deviation 68' is completely attenuated and only later energy from the transmitted wave is detectable at the receiver.

In accordance with the present invention, the method includes the step of repositioning the transmitter and the receiver at different orientations relative to the member to establish different ultrasonic pathways until the selected characteristics of the conditioned electronic waveform are substantially the same as the selected characteristics of the canonical waveform. When this is accomplished, the ultrasonic signal launched from the transmitter has propagated along at least the desired path to the receiver. FIG. 8A shows this repositioning as the loop of steps 82-90 if the determination in line 92 is NO.

It should be noted that if transmitter 26 and receiver 28 are positioned too posterior, a conditioned electronic waveform is obtained that appears similar to the canonical waveform, but an invalid measurement will result. It has been found that a simple test can be performed to determine whether probe 12 is in the proper anterior position. The skin above the path of the ultrasonic signal, i.e., over the anterior cortex 39 is gently pressed. If the probe 12 is in the proper anterior position, the component of the conditioned electronic waveform corresponding to the soft tissue will disappear or diminish appreciably. If the probe 12 is positioned too posterior, the soft tissue component of the conditioned electronic waveform does not change when the skin is depressed.

By making these positional changes, one or more ultrasonic pathways can be established. The reason for this is that the desired path can rarely be found on the first try. Here, the transmitter and receiver must be moved relative to the member until the direct path between them lies along the desired path through the member. When the path between the transmitter and the receiver lies along the desired path the conditioned electronic waveform will have substantially the same characteristics as the canonical waveform shown in FIG. 5.

In accordance with the present invention, the method includes the step of measuring a propagation time for the component of the ultrasonic signal that propagates through the member along the desired path as the time elapsed between launching the ultrasonic signal and receiving the component of the received ultrasonic signal that propagates through the member along the desired path. As embodied herein, and shown in FIG. 8, the method includes the step of determining the propagation time between transmission of the ultrasonic signal and time $t_c$ (step 94).

An apparatus to carry out the method of the present invention includes computing means, which further may also include CPU 19, for performing such calculation using a different program from the comparison program. In the calculation program, CPU 19 first determines the time (the "command time") at which the command is given to excitation-generator 104 to cause transmitter 26 to transmit an ultrasonic signal into the member 32. CPU 19 next determines the time (the "received time") at which the component of the received ultrasonic signal that propagates through the member along desired path 25 arrives at receiver 28. In determining the receive time, the time a which breakpoint 66 is detected by receiver 28 may not be the time at which the component of the received ultrasonic signal that has propagateed through the member along desired path 25 is received by receiver 28. As explained in reference to FIGS. 4a–4d, the breakpoint 66 may be the time at which the component of the ultrasonic signal that has propagated through the anterior cortex arrives. Thus, the actual arrival time of the component that has propagated along the desired path must be determined indirectly or estimated.

CPU 19 preferably estimates the time of receiving the component of the received ultrasonic signal that propagates through the member along the desired path by identifying a first deviation of the received ultrasonic signal from a baseline and identifying a point in time at which the received ultrasonic signal first has an amplitude of zero following the first deviation. The zero amplitude point is an estimate of the time when the component of the received ultrasonic signal that propagates through the member along the desired path is received and is relatively unaffected by the presence or absence of the component that propagates through the anterior cortex. CPU 19 estimates the arrival time of the component of the received ultrasonic signal that propagates through the member along the desired path by detecting the time of receiving the end of first half-cycle 68. The end of first half cycle 68 is the first zero amplitude point 70 and occurs, as shown in FIGS. 4b and 4c at $t_0$.

Preferably, CPU 19 identifies the first deviation, when it is less than a positive threshold value and less than a negative threshold value. As discussed above, and as embodied herein, first deviation 68 is the first excursion of a conditioned electronic waveform from baseline 64. This is the point where the first energy is received by receiver 28. It has been found that some human patellae may exhibit a small initial positive deviation. If this initial positive deviation is sufficiently small, it can safely be disregarded. If, however, the initial positive deviation is above a positive threshold, the conditioned electronic waveform is rejected by CPU 19. Further, the canonical waveform has a first deviation more negative than a predetermined negative threshold value. If the first deviation is less negative than the negative threshold value, the conditioned electronic waveform is rejected by CPU 19. Thus, as discussed in reference to FIGS. 11–13, it can be assumed that the received ultrasonic signal has been neither refractively bent nor subject to phase cancellation at the receiving transducer and that it has traversed the desired path.

In accordance with the present invention, the method includes the step of computing a value for the apparent velocity of the component of the received ultrasonic signal that propagates through the member along the desired path from the measured propagation time and a determined distance between the receiver and said transmitter, the apparent velocity being related to the strength of the member (step 96).

To derive the apparent velocity of sound through a bone requires knowledge or measurement of the distance traveled. The distance divided by the propagation time determined in step 94 yields what is referred to here as the apparent speed of sound. The term "apparent" signifies that the speed of sound represents a composite of all the media traversed: soft tissue, adipose and connective tissues and bone. What is sought is the true velocity of sound in bone, which is the distance traveled through bone by an ultrasonic signal divided by its time of travel. The designation "apparent velocity" reflects the fact that the measurement is an approximation to the "true velocity" of the bone. Under certain conditions, such as, for example, where the thickness of the soft tissue surrounding the bone is sufficiently small, the true velocity is nearly equal to the apparent velocity of sound. Such conditions obtain for the human patella.

Probe 12 includes distance measuring means to measure the distance between transmitter 26 and receiver 28. As embodied herein, distance measuring means includes a digital caliper 30 that provides a digital distance signal, indicative of the distance between transmitter 26 and receiver 28. The distance signal, which is sent along a line 100 to CPU 19, is generated in the following manner. Transmitter 26 is joined to scale 29 through first bar 31. Receiver 28 is joined to slide 27 through second bar 33. As receiver 28 is moved from the origin point (shown in phantom outline in FIG. 7) to the opposite side of member 32 from transmitter 26, it slides along slide 27 and generates a distance signal in proportion to the distance 'd' it moves along the slide. This distance signal is sent along line 100 to CPU 19.

As embodied herein, and shown in FIG. 8, a method in accordance with the present invention includes the step of determining risk of loss of bone strength or risk of disease by comparing the velocity to those of comparable normal or diseased persons (step 98). "Comparable subjects" are those of for example, comparable age, race, and geographical location to he person whose bone strength is being determined. As discussed, the velocity of the ultrasonic signal through the member 32 along the desired path 25 is related to the strength of the member. Specifically referring to equation 5:

$$V = \sqrt{K * r}$$

For diagnostic utility, neither r nor K need be directly computed. The velocity, V, is related to both the bone quality factor, K, and to density, r, and since a decline in either results in loss of strength due to disease, a decline in velocity is indicative of disease and loss of strength. Furthermore, if one determines the density of bone, r, the bone quality factor K can be directly computed. One can determine the risk of loss of the strength of the bone by relating the velocity along the desired path through the member to velocities in a given patient's population group. As embodied herein, this comparison is performed by CPU 19.

Alternatively, the density of bone along the desired path can be determined by, for example, an X-ray technique and the value of K computed. The strength of the bone along the desired path can then be determined by relating the computed value of K to the values of K in a given patient's population group. As embodied herein, the density, r, along the desired path can be entered into CPU 19 through keyboard 22, and the value of K can be computed by CPU 19 and compared by CPU 19 with known values of K.

The velocity of an ultrasonic signal measured along a desired path, such as the upper-central portion of the patella, yields information about the elastic modulus, breaking strength and mass of bone at that site. Such information possesses a significant relationship to the quality or health of bone at the patella and at other sites, such as, the vertebrae.

It will be apparent to those skilled in the art that various modifications and variations can be made in the apparatus and method for ultrasonic analysis of bone strength in vivo of the present invention without departing from the scope or spirit of the invention. Thus, it is intended that the present invention cover the modifications and variations of this invention provided they come within the scope of the appended claims and their equivalents.

What is claimed is:

1. A method for directing an ultrasonic signal along a desired ultrasonic path through a member, the ultrasonic signal being capable of propagating along a plurality of ultrasonic paths and the member interacting with ultrasonic signals differently along each of the plurality of paths, the method comprising the steps of:
   (a) positioning an ultrasonic transmitter and an ultrasonic receiver proximate the member to establish a direct ultrasonic path between said transmitter and said receiver approximately along said desired path;
   (b) launching an ultrasonic signal into the member toward the receiver;
   (c) receiving the launched ultrasonic signal after it propagates through the member and producing a received electronic signal representative of the ultrasonic signal received by said receiver;
   (d) signal conditioning said received electronic signal to produce a conditioned electronic waveform;
   (e) comparing selected characteristics of the conditioned electronic waveform with corresponding selected characteristics of a canonical waveform, said canonical waveform being obtained due to the interaction of the member with said launched ultrasonic signal as said launched ultrasonic signal propagates at least along said desired path through the member; and
   (f) repositioning said transmitter and said receiver at different orientations relative to the member to establish different ultrasonic pathways until said selected characteristics of said conditioned electronic waveform are substantially the same as said corresponding selected characteristics of said canonical waveform, thereby indicating that said ultrasonic signal launched from said transmitter has propagated along at least said desired path to said receiver.

2. A method of establishing the strength of a member, comprising the steps of:
   (a) launching an ultrasonic signal through the member from the transmitter;
   (b) receiving at a receiver the ultrasonic signal after it propagates through the member, the received ultrasonic signal including a component that propagates along a desired path through the member and one or more additional components that propagate through the member along one or more other paths at least one of the additional components arriving at the receiver before the component that propagates along the desired path arrives at the receiver;
   (c) determining the time at which the component that propagated along the desired paths is received,
   (d) measuring a propagation time of the component of the ultrasonic signal that propagates along the desired path through the member as the time elapsed between launching the ultrasonic signal and receiving the component of the received ultrasonic signal that propagates through the member along the desired path; and
   (e) computing a value for the apparent velocity of the component of the received ultrasonic signal that propagates through the member along the desired path by dividing a determined distance between said receiver and said transmitter by the measured propagation time, the apparent velocity being related to the strength of the member.

3. A method for directing an ultrasonic signal along a desired path through a member to determine the strength of a member, the ultrasonic signal being capable of propagating along a plurality of ultrasonic paths, including along a desired ultrasonic path through the member with the member interacting with ultrasonic signals differently along each of the plurality of paths, the method comprising the steps of:
   (a) positioning an ultrasonic transmitter and an ultrasonic receiver, separated by an interprobe distance, proximate the member to establish a direct ultrasonic path between said transmitter and said receiver approximately along said desired path;
   (b) launching an ultrasonic signal into the member toward the receiver;
   (c) receiving the launched ultrasonic signal after it propagates through the member and producing a received electronic signal representative of the ultrasonic signal received by said receiver;
   (d) signal conditioning said received electronic signal to produce a conditioned electronic waveform;
   (e) comparing selected characteristics of the conditioned electronic waveform with corresponding selected characteristics of a canonical waveform, said canonical waveform being obtained due to the interaction of the member with said launched ultrasonic signal as said launched ultrasonic signal propagates at least along said desired path through the member;
   (f) repositioning said transmitter and said receiver at different orientations relative to the member to establish different ultrasonic pathways until said selected characteristics of said conditioned electronic waveform are substantially the same as said corresponding selected characteristics of said canonical waveform, thereby indicating that said ultrasonic signal launched from said transmitter has propagated along at least said desired path to said receiver;
   (g) measuring a propagation time for the component of the ultrasonic signal that propagates through the member along the desired path as the time elapsed between launching the ultrasonic signal and receiving the component of the received ultrasonic signal that propagates through the member along the desired path; and (h) computing a value for the apparent velocity of the component of the received ultrasonic signal that propagates through the member along the desired path by dividing said interprobe distance by the measured propagation time, the apparent velocity being related to the strength of the member.

4. A method as recited in claim 1 or 3 wherein said step of launching an ultrasonic signal through the member includes the step of launching an ultrasonic signal having a first half-cycle of a first polarity, and wherein said step of repositioning said transmitter and said receiver is repeated until said conditioned electronic waveform has a first half cycle of said first polarity.

5. A method as recited in claim 1 or 3 wherein said step of positioning said transmitter and said receiver proximate the member includes the step of positioning said transmitter and said receiver on opposing sides of the member.

6. A method as recited in claim 1 or 3 wherein said step of signal conditioning the received electronic waveform includes the step of auto-ranging the amplitude of the received ultrasonic signal to ensure that the amplitude of said received ultrasonic signal is in a preferred range of values.

7. A method as recited in claim 1 or 3 wherein said step of signal conditioning the received ultrasonic waveform includes the step of log compressing the received ultrasonic signal to ensure that the amplitude of said received ultrasonic signal is in a preferred range of values.

8. A method as recited in claim 1 or 3 wherein said step of comparing the selected characteristics of the conditioned and canonical waveforms includes the step of displaying the conditioned waveform on a video display.

9. A method as recited in claim 2 or 3 wherein said step of measuring the propagation time includes the step of estimating the time of receiving the component of the received ultrasonic signal that propagates through the member along the desired path, by:

identifying a first point in time when said conditioned electronic waveform deviates from a baseline value; and identifying a second point in time at which said conditioned electronic waveform first reaches the baseline value following said first point in time, said second point in time serving as an estimate of the time of receiving the component of the received ultrasonic signal that propagates through the member along the desired path.

10. A method as recited in claim 9 wherein said step of identifying a first point in time includes the step of determining a first deviation of said conditioned electronic waveform to be less than a positive threshold value and less than a negative threshold value.

11. A method as recited in claims 1, 2 or 3 wherein said step of launching an ultrasonic signal through the member includes the step of launching an ultrasonic signal through a bone, in vivo, surrounded by soft tissue.

12. A method as recited in claim 11 wherein said receiving step includes the step of receiving an ultrasonic signal that includes a first portion and a second portion, said first portion of said received ultrasonic signal corresponding to a component of the ultrasonic signal that propagates along a path through the bone and the second portion of the received ultrasonic signal corresponding to a component of the ultrasonic signal that propagates along at least a path through said bone and a path through said soft tissue.

13. A method as recited in claim 12 wherein said step of launching an ultrasonic signal through the member includes the step of launching an ultrasonic signal having at least a high frequency component and a low frequency component, said high frequency component propagating along a path through the soft tissue and said low frequency component propagating along a path through the bone.

14. A method as recited in claim 13 wherein said receiving step includes receiving an ultrasonic signal wherein said first portion is characterized by a first frequency range and said second portion is characterized by a second frequency range different than said first frequency range.

15. A method as recited in claim 11 wherein said step of receiving an ultrasonic signal includes the step of receiving a first portion of the ultrasonic signal, the first portion of the ultrasonic signal corresponding to the component of the ultrasonic signal that traverses the desired path.

16. A method as recited in claim 15 wherein said step of receiving an ultrasonic signal includes the step of receiving a second portion of the ultrasonic signal, the second portion of the ultrasonic signal being received prior to receiving the first portion of the ultrasonic signal.

17. A method as recited in claim 16 wherein said step of receiving an ultrasonic signal includes the step of receiving the first portion of the ultrasonic signal which traverses the desired path, wherein the desired path lies along a central core region of a human patella, the central core region lying below an anterior cortex of the human patella.

18. A method as recited in claim 17 wherein said step of receiving an ultrasonic signal includes receiving the second portion of the ultrasonic signal, wherein the second portion of the ultrasonic signal traverses a path that lies along an anterior cortex of a human patella.

19. A method as recited in claim 17 wherein said step of receiving the first portion of the ultrasonic signal which traverses the desired path lying along a central core region of a human patella, wherein the central core region is comprised of less dense bone than the anterior cortex.

20. A method as recited in claims 1 or 3 wherein: said step of launching an ultrasonic signal through the member includes the step of launching an ultrasonic signal through a bone, in vivo, surrounded by soft tissue;

said receiving step includes the step of receiving an ultrasonic signal that includes a first portion and a second portion, said first portion of said received ultrasonic signal corresponding to a component of the ultrasonic signal that propagates along a path through the bone and the second portion of the received ultrasonic signal corresponding to a component of the ultrasonic signal that propagates along at least a path through said bone and a path through said soft tissue; and said comparing step includes the step of attempting to locate first and second portions in said electronic waveform, said first and second portions having first and second distinguishable measured characteristics, respectively, which are similar to said selected characteristics of said canonical waveform.

21. A method as recited in claim 20 wherein said first and second distinguishable characteristics include first and second frequency ranges, respectively, and wherein said location attempting step includes the substeps of:
measuring a first predetermined amount of energy in a first frequency range of said first portion of said electronic waveform; and
measuring a second predetermined amount of energy in a second frequency range of said second portion of said electronic waveform.

22. An apparatus for directing an ultrasonic signal along a desired ultrasonic path through a member, the ultrasonic signal being capable of propagating along a plurality of ultrasonic paths with the member interacting with the ultrasonic signal differently along each of the plurality of paths, the apparatus comprising:
(a) an ultrasonic transmitter and an ultrasonic receiver positioned proximate the member to establish a direct ultrasonic path between said transmitter and said receiver approximately along said desired path, said transmitter including means for launching a launched ultrasonic signal into the member toward the receiver, and said receiver including means for receiving the launched ultrasonic signal after it propagates through the member and producing a received electronic signal representative of the ultrasonic signal received by said receiver;
(b) signal conditioning means in communication with said receiver for adjusting said received electronic signal to form a conditioned electronic waveform; and
(c) comparing means, coupled to said signal conditioning means, for permitting comparison of selected characteristics of the conditioned electronic waveform with corresponding selected characteristics of a canonical waveform, said canonical waveform being obtained due to the interaction of the member with said launched ultrasonic signal as said launched ultrasonic signal propagates at least along the desired path through the member, said comparing means permitting comparison of said selected characteristics of said conditioned electronic waveform with said corresponding selected characteristics of said canonical waveform, whereby said transmitter and said receiver can be repositioned at different orientations relative to the member to establish different ultrasonic pathways -until said selected characteristics of said conditioned electronic waveform are substantially the same as said selected characteristics of said canonical waveform, thereby indicating that said ultrasonic signal launched from said transmitter has propagated along at least said desired path to said receiver.

23. An apparatus for directing an ultrasonic signal along a desired ultrasonic path through a member to establish the strength of the member, the ultrasonic signal being capable of propagating along a plurality of ultrasonic paths with the member interacting with the ultrasonic signal differently along each of the plurality of paths, the apparatus comprising:
(a) an ultrasonic transmitter and an ultrasonic receiver positioned proximate the member to establish a direct ultrasonic path between said transmitter and said receiver approximately along said desired path, said transmitter including means for launching a launched ultrasonic signal into the member toward the receiver, and said receiver including means for receiving the launched ultrasonic signal after it propagates through the member and producing a received electronic signal representative of the ultrasonic signal received by said receiver;
(b) signal conditioning means in communication with said receiver for adjusting said received electronic signal to form a conditioned electronic waveform;
(c) comparing means, coupled to said signal conditioning means, for permitting comparison of selected characteristics of the conditioned electronic waveform with known selected characteristics of a canonical waveform, said canonical waveform being obtained due to the interaction of the member with said launched ultrasonic signal as said launched ultrasonic signal propagates at least along the desired path through the member; and
(d) computing means, responsive to said comparing means, for measuring a propagation time for the desired ultrasonic signal through the member as the time elapsed between the launching of said ultrasonic signal and the receiving of the component of the received ultrasonic signal that propagates through the member along the desired path, and for computing a value for the apparent velocity of the component of the received ultrasonic signal that propagates through the member along the desired path by dividing a determined distance between said receiver and said transmitter by the measured propagation time, said apparent velocity being related to the strength of the member.

24. An apparatus as recited in claim 22 or 23 further including mounting structure coupled to said transmitter and said receiver to allow said transmitter and said receiver to be positioned on either side of the member.

25. An apparatus as recited in claim 22 or 23 wherein said signal conditioning means includes auto-ranging means for ensuring that the amplitude of said received ultrasonic signal is in a range providing for linear operation of the signal conditioning means.

26. An apparatus as recited in claim 22 or 23 wherein said signal conditioning means includes log compressing means for ensuring that the amplitude of said received ultrasonic signal is in a range providing for linear operation of the signal conditioning means.

27. An apparatus as recited in claim 22 or 23 further including means for displaying said conditioned electronic waveform.

28. An apparatus as recited in claim 27 wherein said display means includes a video display.

29. An apparatus as recited in claim 23 wherein said computing means includes means for estimating the time of receiving the component of the received ultrasonic signal that propagates through the member along the desired path by:
identifying a first point in time when said conditioned electronic waveform deviates from a baseline value; and
identifying a second point in time at which said conditioned electronic waveform first reaches the baseline value following said first point in time, said second point in time serving as an estimate of the time of receiving the component of the received ultrasonic signal that propagates through the member along the desired path.

30. An apparatus as recited in claim 29 wherein said computing means further includes means for determining when said a first deviation of said conditioned electronic waveform is less than a positive threshold value and less than a negative threshold value.

31. An apparatus as recited in claim 22 or 23, wherein said transmitter includes means for transmitting an ultrasonic signal that includes at least a high frequency component that propagates along a path through soft tissue and a low frequency component that propagates along a path through bone when said ultrasonic transmitter and said ultrasonic receiver are positioned proximate a bone, in vivo, surrounded by soft tissue.

32. An apparatus as recited in claim 31 wherein said comparing means includes means for locating first and second portions of said conditioned electronic waveform which are similar to corresponding first and second portions of said canonical waveform.

* * * * *